United States Patent
Huang et al.

(10) Patent No.: US 8,658,394 B2
(45) Date of Patent: Feb. 25, 2014

(54) METHODS, CELLS AND SYSTEMS FOR INCORPORATING NON-CANONICAL AMINO ACIDS INTO PROTEINS

(75) Inventors: Ying Huang, College Station, TX (US); Wenshe Liu, College Station, TX (US)

(73) Assignee: Waterstone Pharmaceuticals, Wuhan (CN)

( * ) Notice: Subject to any disclaimer, the term of this patent is extended or adjusted under 35 U.S.C. 154(b) by 24 days.

(21) Appl. No.: 13/353,106

(22) Filed: Jan. 18, 2012

(65) Prior Publication Data

US 2012/0237971 A1 Sep. 20, 2012

Related U.S. Application Data

(60) Provisional application No. 61/438,743, filed on Feb. 2, 2011.

(51) Int. Cl.
*C12P 21/00* (2006.01)
*C12N 1/21* (2006.01)
*C12N 15/63* (2006.01)
*C12N 1/00* (2006.01)

(52) U.S. Cl.
USPC ............... 435/68.1; 435/252.33; 435/317.1; 435/320.1; 435/69.1

(58) Field of Classification Search
None
See application file for complete search history.

(56) References Cited

U.S. PATENT DOCUMENTS 7,790,847 B2 * 9/2010 Wang et al. ............... 530/350
8,114,627 B2 * 2/2012 Liu et al. .................. 435/69.1

OTHER PUBLICATIONS

Huang et al. A convinient Method for genetic incorporation of multiple non-canonical amino acids into one protein in *Essherichia coli* Mol. BioSyst., 2010, 6, 683-686.*
Bouakaz et al 2006 The Role of Ribosomal Protein L11 in Class I Release Factor-mediated Translation Termination and Translational Accuracy. Journal of Biological Chemistry, 281, 4548-4556.*
The Role of Ribosomal Protein L11 in Class I Release Factor-mediated Translation Termination and Translational Accuracy.Journal of Biological Chemistry, 281, 4548-4556.*

* cited by examiner

*Primary Examiner* — Kagnew H Gebreyesus
(74) *Attorney, Agent, or Firm* — Novak Druce Connolly Bove + Quigg LLP

(57) ABSTRACT

The present disclosure pertains to methods of incorporating one or more non-canonical amino acids into a protein during a translation of the protein in bacterial cells. The present disclosure also pertains to methods of incorporating one or more non-canonical amino acids into a protein during an in vitro translation of the protein. In additional embodiments, the present disclosure pertains to isolated bacterial cells and in vitro translation systems (e.g., cell-free extract systems) for incorporating one or more non-canonical amino acids into a protein during a translation of the protein.

15 Claims, 4 Drawing Sheets

```
                        SEQUENCE LISTING

<160> NUMBER OF SEQ ID NOS: 43

<210> SEQ ID NO 1
<211> LENGTH: 31
<212> TYPE: DNA
<213> ORGANISM: Artificial Sequence
<220> FEATURE:
<223> OTHER INFORMATION: Primer

<400> SEQUENCE: 1
gaggaatccc atatggataa aaaccatta g                                       31

<210> SEQ ID NO 2
<211> LENGTH: 29
<212> TYPE: DNA
<213> ORGANISM: Artificial Sequence
<220> FEATURE:
<223> OTHER INFORMATION: Primer

<400> SEQUENCE: 2
cgtttgaaac tgcagttaca gattggttg                                         29

<210> SEQ ID NO 3
<211> LENGTH: 31
<212> TYPE: DNA
<213> ORGANISM: Artificial Sequence
<220> FEATURE:
<223> OTHER INFORMATION: Primer

<400> SEQUENCE: 3
gaggaatccc atatggataa aaaccatta g                                       31

<210> SEQ ID NO 4
<211> LENGTH: 40
<212> TYPE: DNA
<213> ORGANISM: Artificial Sequence
<220> FEATURE:
<223> OTHER INFORMATION: Primer

<400> SEQUENCE: 4
aaattattga tatcctcgcc cgaaaccta catcgtttgc                              40

<210> SEQ ID NO 5
<211> LENGTH: 36
<212> TYPE: DNA
<213> ORGANISM: Artificial Sequence
<220> FEATURE:
<223> OTHER INFORMATION: Primer
```

```
<400> SEQUENCE: 5
gatgtagggt tcgggcgag gatatcaata attttc                          36

<210> SEQ ID NO 6
<211> LENGTH: 37
<212> TYPE: DNA
<213> ORGANISM: Artificial Sequence
<220> FEATURE:
<223> OTHER INFORMATION: Primer

<400> SEQUENCE: 6
gttgaaaata gtcggggcaa ccattggcct caagcag                        37

<210> SEQ ID NO 7
<211> LENGTH: 39
<212> TYPE: DNA
<213> ORGANISM: Artificial Sequence
<220> FEATURE:
<223> OTHER INFORMATION: Primer

<400> SEQUENCE: 7
gccccgacta ttttcaacta tgcgcgaaaa ctcgatagg                      39

<210> SEQ ID NO 8
<211> LENGTH: 30
<212> TYPE: DNA
<213> ORGANISM: Artificial Sequence
<220> FEATURE:
<223> OTHER INFORMATION: Primer

<400> SEQUENCE: 8
ccgaacccat ctgaaagaag ttcaccatag                                30

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
ctatggtgaa cttctttcag atgggttcgg                                30

<210> SEQ ID NO 10
<211> LENGTH: 29
<212> TYPE: DNA
<213> ORGANISM: Artificial Sequence
<220> FEATURE:
<223> OTHER INFORMATION: Primer

<400> SEQUENCE: 10
cgtttgaaac tgcagttaca gattggttg                                 29

<210> SEQ ID NO 11
<211> LENGTH: 35
<212> TYPE: DNA
<213> ORGANISM: Artificial Sequence
<220> FEATURE:
<223> OTHER INFORMATION: Primer

<400> SEQUENCE: 11
cccgggatcc cccatcaaaa aaatattctc aacat                          35

<210> SEQ ID NO 12
<211> LENGTH: 45
<212> TYPE: DNA
```

```
<213> ORGANISM: Artificial Sequence
<220> FEATURE:
<223> OTHER INFORMATION: Primer

<400> SEQUENCE: 12
ttacaagtat tacacaaagt tttttatgtt gagaatattt ttttg          45

<210> SEQ ID NO 13
<211> LENGTH: 50
<212> TYPE: DNA
<213> ORGANISM: Artificial Sequence
<220> FEATURE:
<223> OTHER INFORMATION: Primer

<400> SEQUENCE: 13
actttgtgta atacttgtaa cgctgaatcc ggaaacctga tcatgtagat      50

<210> SEQ ID NO 14
<211> LENGTH: 51
<212> TYPE: DNA
<213> ORGANISM: Artificial Sequence
<220> FEATURE:
<223> OTHER INFORMATION: Primer

<400> SEQUENCE: 14
ctaacccggc tgaacggatt tagagtccat tcgatctaca tgatcaggtt t    51

<210> SEQ ID NO 15
<211> LENGTH: 50
<212> TYPE: DNA
<213> ORGANISM: Artificial Sequence
<220> FEATURE:
<223> OTHER INFORMATION: Primer

<400> SEQUENCE: 15
tcagccgggt tagattcccg gggtttccgc cactgcccat ccttagcgaa      50

<210> SEQ ID NO 16
<211> LENGTH: 43
<212> TYPE: DNA
<213> ORGANISM: Artificial Sequence
<220> FEATURE:
<223> OTHER INFORMATION: Primer

<400> SEQUENCE: 16
gaacccagat cttaaaaaaa atccttagct ttcgctaagg atg             43

<210> SEQ ID NO 17
<211> LENGTH: 33
<212> TYPE: DNA
<213> ORGANISM: Artificial Sequence
<220> FEATURE:
<223> OTHER INFORMATION: Primer

<400> SEQUENCE: 17
gatataacat gtcagataaa aaaccattag atg                        33

<210> SEQ ID NO 18
<211> LENGTH: 33
<212> TYPE: DNA
<213> ORGANISM: Artificial Sequence
<220> FEATURE:
<223> OTHER INFORMATION: Primer

<400> SEQUENCE: 18
gtcgacctgc agttacagat tggttgaaat ccc                        33
```

<210> SEQ ID NO 19
<211> LENGTH: 31
<212> TYPE: DNA
<213> ORGANISM: Artificial Sequence
<220> FEATURE:
<223> OTHER INFORMATION: Primer

<400> SEQUENCE: 19
gaaggagata tacatatgag taaaggagaa g                          31

<210> SEQ ID NO 20
<211> LENGTH: 35
<212> TYPE: DNA
<213> ORGANISM: Artificial Sequence
<220> FEATURE:
<223> OTHER INFORMATION: Primer

<400> SEQUENCE: 20
gactcgaggg taccttagtg atggtgatgg tgatg                      35

<210> SEQ ID NO 21
<211> LENGTH: 27
<212> TYPE: DNA
<213> ORGANISM: Artificial Sequence
<220> FEATURE:
<223> OTHER INFORMATION: Primer

<400> SEQUENCE: 21
gctagatctg gaaacctgat gtagatc                               27

<210> SEQ ID NO 22
<211> LENGTH: 25
<212> TYPE: DNA
<213> ORGANISM: Artificial Sequence
<220> FEATURE:
<223> OTHER INFORMATION: Primer

<400> SEQUENCE: 22
gatactagtt ggcggaaacc ccggg                                 25

<210> SEQ ID NO 23
<211> LENGTH: 34
<212> TYPE: DNA
<213> ORGANISM: Artificial Sequence
<220> FEATURE:
<223> OTHER INFORMATION: Primer

<400> SEQUENCE: 23
ctttcgaaag ggcagactat gtcgacaggt aatg                       34

<210> SEQ ID NO 24
<211> LENGTH: 34
<212> TYPE: DNA
<213> ORGANISM: Artificial Sequence
<220> FEATURE:
<223> OTHER INFORMATION: Primer

<400> SEQUENCE: 24
cattacctgt cgacatagtc tgcccttttcg aaag                      34

<210> SEQ ID NO 25
<211> LENGTH: 36
<212> TYPE: DNA
<213> ORGANISM: Artificial Sequence
<220> FEATURE:
<223> OTHER INFORMATION: Primer

<400> SEQUENCE: 25
atcgccaatt ggagtattct attgataatg gtctgc                                36

<210> SEQ ID NO 26
<211> LENGTH: 36
<212> TYPE: DNA
<213> ORGANISM: Artificial Sequence
<220> FEATURE:
<223> OTHER INFORMATION: Primer

<400> SEQUENCE: 26
gcagaccatt atcaatagaa tactccaatt ggcgat                                36

<210> SEQ ID NO 27
<211> LENGTH: 33
<212> TYPE: DNA
<213> ORGANISM: Artificial Sequence
<220> FEATURE:
<223> OTHER INFORMATION: Primer

<400> SEQUENCE: 27
ggagatatac atatgaccaa gaccccgccg gca                                   33

<210> SEQ ID NO 28
<211> LENGTH: 30
<212> TYPE: DNA
<213> ORGANISM: Artificial Sequence
<220> FEATURE:
<223> OTHER INFORMATION: Primer

<400> SEQUENCE: 28
gtcgtcggta ccttagtcct ccactaccag                                       30

<210> SEQ ID NO 29
<211> LENGTH: 72
<212> TYPE: DNA
<213> ORGANISM: Escherichia coli

<400> SEQUENCE: 29
ggaaacctga tcatgtagat cgaatggact ctaaatccgt tcagccgggt tagattcccg      60
gggtttccgc ca                                                         72

<210> SEQ ID NO 30
<211> LENGTH: 54
<212> TYPE: DNA
<213> ORGANISM: Artificial Sequence
<220> FEATURE:
<223> OTHER INFORMATION: promoter

<400> SEQUENCE: 30
cccatcaaaa aaatattctc aacataaaaa actttgtgta atacttgtaa cgct            54

<210> SEQ ID NO 31
<211> LENGTH: 30
<212> TYPE: DNA
<213> ORGANISM: Artificial Sequence
<220> FEATURE:
<223> OTHER INFORMATION: Teerminator

<400> SEQUENCE: 31
atccttagcg aaagctaagg atttttttta                                      30

<210> SEQ ID NO 32
<211> LENGTH: 1263
<212> TYPE: DNA

<213> ORGANISM: Escherichia coli

<400> SEQUENCE: 32

```
atgtcagata aaaaaccatt agatgtttta atatctgcga ccgggctctg gatgtccagg      60
actggcacgc tccacaaaat caagcaccat gaggtctcaa gaagtaaaat atacattgaa     120
atggcgtgtg gagaccatct tgttgtgaat aattccagga gttgtagaac agccagagca     180
ttcagacatc ataagtacag aaaaacctgc aaacgatgta gggtttcggg cgaggatatc     240
ataaatttc  tcacaagatc aaccgaaagc aaaaacagtg tgaaagttag ggtagttct      300
gctccaaagg tcaaaaaagc tatgccgaaa tcagtttcaa gggctccgaa gcctctggaa     360
aattctgttt ctgcaaaggc atcaacgaac acatccagat ctgtaccttc gcctgcaaaa     420
tcaactccaa attcgtctgt tcccgcatcg gctcctgctc cttcacttac aagaagccag     480
cttgataggg ttgaggctct cttaagtcca gaggataaaa tttctctgaa tatggcaaag     540
cctttcagga aacttgagcc tgaacttgtg acaagaagaa aaacgatttt tcagcggctc     600
tataccaatg atagagaaga ctacctcggt aaactcgaac gtgatattac gaaattttc     660
gtagaccggg ttttctggag ataaagtct cctatcctta ttccggcgga atacgtggag     720
agaatgggta ttaataatga tactgaactt tcaaaacaga tcttccgggt ggataaaaat     780
ctctgcttga ggccaatggt tgccccgact attttcaact atgcgcgaaa actcgatagg     840
attttaccag gcccaataaa aattttcgaa gtcggaccct gttaccggaa agagtctgac     900
ggcaaagagc acctggaaga atttactatg gtgaacttct ttcagatggg ttcgggatgt     960
actcgggaaa atcttgaagc tctcatcaaa gagtttctgg actatctgga aatcgacttc    1020
gaaatcgtag gagattcctg tatggtctat ggggatactc ttgatataat gcacggggac    1080
ctggagcttt cttcggcagt cgtcgggcca gtttctcttg atagagaatg gggtattgac    1140
aaaccatgga taggtgcagg ttttggtctt gaacgcttgc tcaaggttat gcacggcttt    1200
aaaaacatta gagggcatc  aaggtccgaa tcttactata tgggatttc  aaccaatctg    1260
taa                                                                 1263
```

<210> SEQ ID NO 33
<211> LENGTH: 222
<212> TYPE: DNA
<213> ORGANISM: Escherichia coli

<400> SEQUENCE: 33

```
atgaccaaga ccccgccggc agcagttctg ctgaaaaaag cggctggtat caagtctggt     60
tccggtaagc cgaacaaaga caaagtgggt aaaatttccc gcgctcagct gcaggaaatc    120
gcgcagacca agctgccgca catgactggt gccgacattg aagcgatgac tcgctccatc    180
gaaggtactg cacgttccat gggcctggta gtggaggact aa                       222
```

<210> SEQ ID NO 34
<211> LENGTH: 741
<212> TYPE: DNA
<213> ORGANISM: Aequorea victoria

<400> SEQUENCE: 34

```
atgagtaaag gagaagaact tttcactgga gttgtcccaa ttcttgttga attagatggt     60
gatgttaatg ggcacaaatt ttctgtcagt ggagagggtg aaggtgatgc aacatacgga    120
aaacttaccc ttaaatttat ttgcactact ggaaaactac ctgttccatg gccaacactt    180
gtcactactt tctcttatgg tgttcaatgc ttttcccgtt atccggatca catgaaacgg    240
```

| | |
|---|---|
| catgactttt tcaagagtgc catgcccgaa ggttatgtac aggaacgcac tatatctttc | 300 |
| aaagatgacg ggaactacaa gacgcgtgct gaagtcaagt ttgaaggtga tacccttgtt | 360 |
| aatcgtatcg agttaaaagg tattgatttt aaagaagatg aaacattct cggacacaaa | 420 |
| ctcgagtaca actataactc acactaggta tacatcacgg cagacaaaca aaagaatgga | 480 |
| atcaaagcta acttcaaaat tcgccacaac attgaagatg gatccgttca actagcagac | 540 |
| cattatcaac aaaatactcc aattggcgat ggccctgtcc ttttaccaga caaccattac | 600 |
| ctgtcgacac aatctgccct ttcgaaagat cccaacgaaa agcgtgacca catggtcctt | 660 |
| cttgagtttg taactgctgc tgggattaca catggcatgg atgaactcta caaagagctc | 720 |
| catcaccatc accatcacta a | 741 |

<210> SEQ ID NO 35
<211> LENGTH: 741
<212> TYPE: DNA
<213> ORGANISM: Aequorea victoria

<400> SEQUENCE: 35

| | |
|---|---|
| atgagtaaag gagaagaact tttcactgga gttgtcccaa ttcttgttga attagatggt | 60 |
| gatgttaatg ggcacaaatt ttctgtcagt ggagagggtg aaggtgatgc aacatacgga | 120 |
| aaacttaccc ttaaatttat ttgcactact ggaaaactac ctgttccatg gccaacactt | 180 |
| gtcactactt tctcttatgg tgttcaatgc ttttcccgtt atccggatca catgaaacgg | 240 |
| catgactttt tcaagagtgc catgcccgaa ggttatgtac aggaacgcac tatatctttc | 300 |
| aaagatgacg ggaactacaa gacgcgtgct gaagtcaagt ttgaaggtga tacccttgtt | 360 |
| aatcgtatcg agttaaaagg tattgatttt aaagaagatg aaacattct cggacacaaa | 420 |
| ctcgagtaca actataactc acactaggta tacatcacgg cagacaaaca aaagaatgga | 480 |
| atcaaagcta acttcaaaat tcgccacaac attgaagatg gatccgttca actagcagac | 540 |
| cattatcaac aaaatactcc aattggcgat ggccctgtcc ttttaccaga caaccattac | 600 |
| ctgtcgacat agtctgccct ttcgaaagat cccaacgaaa agcgtgacca catggtcctt | 660 |
| cttgagtttg taactgctgc tgggattaca catggcatgg atgaactcta caaagagctc | 720 |
| catcaccatc accatcacta a | 741 |

<210> SEQ ID NO 36
<211> LENGTH: 741
<212> TYPE: DNA
<213> ORGANISM: Aequorea victoria

<400> SEQUENCE: 36

| | |
|---|---|
| atgagtaaag gagaagaact tttcactgga gttgtcccaa ttcttgttga attagatggt | 60 |
| gatgttaatg ggcacaaatt ttctgtcagt ggagagggtg aaggtgatgc aacatacgga | 120 |
| aaacttaccc ttaaatttat ttgcactact ggaaaactac ctgttccatg gccaacactt | 180 |
| gtcactactt tctcttatgg tgttcaatgc ttttcccgtt atccggatca catgaaacgg | 240 |
| catgactttt tcaagagtgc catgcccgaa ggttatgtac aggaacgcac tatatctttc | 300 |
| aaagatgacg ggaactacaa gacgcgtgct gaagtcaagt ttgaaggtga tacccttgtt | 360 |
| aatcgtatcg agttaaaagg tattgatttt aaagaagatg aaacattct cggacacaaa | 420 |
| ctcgagtaca actataactc acactaggta tacatcacgg cagacaaaca aaagaatgga | 480 |
| atcaaagcta acttcaaaat tcgccacaac attgaagatg gatccgttca actagcagac | 540 |
| cattatcaat agaatactcc aattggcgat ggccctgtcc ttttaccaga caaccattac | 600 |

```
ctgtcgacat agtctgccct ttcgaaagat cccaacgaaa agcgtgacca catggtcctt    660
cttgagtttg taactgctgc tgggattaca catggcatgg atgaactcta caaagagctc    720
catcaccatc accatcacta a                                              741
```

<210> SEQ ID NO 37
<211> LENGTH: 747
<212> TYPE: DNA
<213> ORGANISM: Aequorea victoria

<400> SEQUENCE: 37

```
atggcataga gtaaaggaga agaacttttc actggagttg tcccaattct tgttgaatta     60
gatggtgatg ttaatgggca caaattttct gtcagtggag agggtgaagg tgatgcaaca    120
tacggaaaac ttacccttaa atttatttgc actactggaa aactacctgt tccatggcca    180
acacttgtca ctactttctc ttatggtgtt caatgctttt cccgttatcc ggatcacatg    240
aaacggcatg actttttcaa gagtgccatg cccgaaggtt atgtacagga acgcactata    300
tctttcaaag atgacgggaa ctacaagacg cgtgctgaag tcaagtttga aggtgatacc    360
cttgttaatc gtatcgagtt aaaaggtatt gattttaaag aagatggaaa cattctcgga    420
cacaaactcg agtacaacta taactcacac taggtataca tcacggcaga caaacaaaag    480
aatggaatca aagctaactt caaaattcgc cacaacattg aagatggatc cgttcaacta    540
gcagaccatt atcaacaaaa tactccaatt ggcgatggcc ctgtcctttt accagacaac    600
cattacctgt cgacatagtc tgccctttcg aaagatccca acgaaagcg tgaccacatg    660 gtccttcttg agtttgtaac tgctgctggg attacacatg gcatggatga actctacaaa    720
gagctccatc accatcacca tcactaa                                        747
```

<210> SEQ ID NO 38
<211> LENGTH: 420
<212> TYPE: PRT
<213> ORGANISM: Escherichia coli

<400> SEQUENCE: 38

```
Met Ser Asp Lys Lys Pro Leu Asp Val Leu Ile Ser Ala Thr Gly Leu
1               5                   10                  15

Trp Met Ser Arg Thr Gly Thr Leu His Lys Ile Lys His His Glu Val
            20                  25                  30

Ser Arg Ser Lys Ile Tyr Ile Glu Met Ala Cys Gly Asp His Leu Val
        35                  40                  45

Val Asn Asn Ser Arg Ser Cys Arg Thr Ala Arg Ala Phe Arg His His
    50                  55                  60

Lys Tyr Arg Lys Thr Cys Lys Arg Cys Arg Val Ser Gly Glu Asp Ile
65                  70                  75                  80

Asn Asn Phe Leu Thr Arg Ser Thr Glu Ser Lys Asn Ser Val Lys Val
                85                  90                  95

Arg Val Val Ser Ala Pro Lys Val Lys Lys Ala Met Pro Lys Ser Val
            100                 105                 110

Ser Arg Ala Pro Lys Pro Leu Glu Asn Ser Val Ser Ala Lys Ala Ser
        115                 120                 125

Thr Asn Thr Ser Arg Ser Val Pro Ser Pro Ala Lys Ser Thr Pro Asn
    130                 135                 140

Ser Ser Val Pro Ala Ser Ala Pro Ala Pro Ser Leu Thr Arg Ser Gln
145                 150                 155                 160

Leu Asp Arg Val Glu Ala Leu Leu Ser Pro Glu Asp Lys Ile Ser Leu
                165                 170                 175
```

Asn Met Ala Lys Pro Phe Arg Glu Leu Glu Pro Glu Leu Val Thr Arg
            180                 185                 190

Arg Lys Asn Asp Phe Gln Arg Leu Tyr Thr Asn Asp Arg Glu Asp Tyr
        195                 200                 205

Leu Gly Lys Leu Glu Arg Asp Ile Thr Lys Phe Phe Val Asp Arg Gly
210                 215                 220

Phe Leu Glu Ile Lys Ser Pro Ile Leu Ile Pro Ala Glu Tyr Val Glu
225                 230                 235                 240

Arg Met Gly Ile Asn Asn Asp Thr Glu Leu Ser Lys Gln Ile Phe Arg
                245                 250                 255

Val Asp Lys Asn Leu Cys Leu Arg Pro Met Val Ala Pro Thr Ile Phe
            260                 265                 270

Asn Tyr Ala Arg Lys Leu Asp Arg Ile Leu Pro Gly Pro Ile Lys Ile
        275                 280                 285

Phe Glu Val Gly Pro Cys Tyr Arg Lys Glu Ser Asp Gly Lys Glu His
290                 295                 300

Leu Glu Glu Phe Thr Met Val Asn Phe Phe Gln Met Gly Ser Gly Cys
305                 310                 315                 320

Thr Arg Glu Asn Leu Glu Ala Leu Ile Lys Glu Phe Leu Asp Tyr Leu
                325                 330                 335

Glu Ile Asp Phe Glu Ile Val Gly Asp Ser Cys Met Val Tyr Gly Asp
            340                 345                 350

Thr Leu Asp Ile Met His Gly Asp Leu Glu Leu Ser Ser Ala Val Val
        355                 360                 365

Gly Pro Val Ser Leu Asp Arg Glu Trp Gly Ile Asp Lys Pro Trp Ile
370                 375                 380

Gly Ala Gly Phe Gly Leu Glu Arg Leu Leu Lys Val Met His Gly Phe
385                 390                 395                 400

Lys Asn Ile Lys Arg Ala Ser Arg Ser Glu Ser Tyr Tyr Asn Gly Ile
                405                 410                 415

Ser Thr Asn Leu
            420

<210> SEQ ID NO 39
<211> LENGTH: 73
<212> TYPE: PRT
<213> ORGANISM: Escherichia coli

<400> SEQUENCE: 39

Met Thr Lys Thr Pro Pro Ala Ala Val Leu Leu Lys Lys Ala Ala Gly
1               5                   10                  15

Ile Lys Ser Gly Ser Gly Lys Pro Asn Lys Asp Lys Val Gly Lys Ile
            20                  25                  30

Ser Arg Ala Gln Leu Gln Glu Ile Ala Gln Thr Lys Ala Ala Asp Met
        35                  40                  45

Thr Gly Ala Asp Ile Glu Ala Met Thr Arg Ser Ile Glu Gly Thr Ala
    50                  55                  60

Arg Ser Met Gly Leu Val Val Glu Asp
65                  70

<210> SEQ ID NO 40
<211> LENGTH: 247
<212> TYPE: PRT
<213> ORGANISM: Aequorea victoria
<220> FEATURE:
<221> NAME/KEY: misc_feature
<222> LOCATION: (150)..(150)

-continued

<223> OTHER INFORMATION: Xaa can be any naturally occurring amino acid

<400> SEQUENCE: 40

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Lys Xaa Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Lys Glu
225                 230                 235                 240

Leu His His His His His His
                245
```

<210> SEQ ID NO 41
<211> LENGTH: 247
<212> TYPE: PRT
<213> ORGANISM: Aequorea victoria
<220> FEATURE:
<221> NAME/KEY: misc_feature
<222> LOCATION: (150)..(150)
<223> OTHER INFORMATION: Xaa can be any naturally occurring amino acid

<400> SEQUENCE: 41

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
```

-continued

```
            85                  90                  95
Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
            130                 135                 140

Tyr Asn Ser His Lys Xaa Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Lys Ser Ala Leu
            195                 200                 205

Ser Lys Asp Pro Asn Glu Lys Arg Asp His Met Val Leu Leu Glu Phe
            210                 215                 220

Val Thr Ala Ala Gly Ile Thr His Gly Met Asp Glu Leu Tyr Lys Glu
225                 230                 235                 240

Leu His His His His His His
            245
```

<210> SEQ ID NO 42
<211> LENGTH: 248
<212> TYPE: PRT
<213> ORGANISM: Aequorea victoria
<220> FEATURE:
<221> NAME/KEY: misc_feature
<222> LOCATION: (150)..(150)
<223> OTHER INFORMATION: Xaa can be any naturally occurring amino acid
<220> FEATURE:
<221> NAME/KEY: misc_feature
<222> LOCATION: (186)..(186)
<223> OTHER INFORMATION: Xaa can be any naturally occurring amino acid

<400> SEQUENCE: 42

```
Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
            50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
            85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
            115                 120                 125

Asp Phe Lys Glu Asp Gly Asn Ile Leu Gly His Lys Leu Glu Tyr Asn
            130                 135                 140

Tyr Asn Ser His Lys Xaa Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175
```

```
Val Gln Leu Ala Asp His Tyr Gln Lys Xaa Asn Thr Pro Ile Gly Asp
            180                 185                 190
Gly Pro Val Leu Leu Pro Asp Asn His Tyr Leu Ser Thr Lys Ser Ala
        195                 200                 205
Leu Ser Lys Asp Pro Asn Glu Lys Arg Asp His Met Val Leu Leu Glu
210                 215                 220
Phe Val Thr Ala Ala Gly Ile Thr His Gly Met Asp Glu Leu Tyr Lys
225                 230                 235                 240
Glu Leu His His His His His His
            245
```

```
<210> SEQ ID NO 43
<211> LENGTH: 250
<212> TYPE: PRT
<213> ORGANISM: Aequorea victoria
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (153)..(153)
<223> OTHER INFORMATION: Xaa can be any naturally occurring amino acid

<400> SEQUENCE: 43

Met Ala Lys Xaa Ser Lys Gly Glu Glu Leu Phe Thr Gly Val Val Pro
1               5                   10                  15
Ile Leu Val Glu Leu Asp Gly Asp Val Asn Gly His Lys Phe Ser Val
            20                  25                  30
Ser Gly Glu Gly Glu Gly Asp Ala Thr Tyr Gly Lys Leu Thr Leu Lys
        35                  40                  45
Phe Ile Cys Thr Thr Gly Lys Leu Pro Val Pro Trp Pro Thr Leu Val
    50                  55                  60
Thr Thr Phe Ser Tyr Gly Val Gln Cys Phe Ser Arg Tyr Pro Asp His
65                  70                  75                  80
Met Lys Arg His Asp Phe Phe Lys Ser Ala Met Pro Glu Gly Tyr Val
                85                  90                  95
Gln Glu Arg Thr Ile Ser Phe Lys Asp Asp Gly Asn Tyr Lys Thr Arg
            100                 105                 110
Ala Glu Val Lys Phe Glu Gly Asp Thr Leu Val Asn Arg Ile Glu Leu
        115                 120                 125
Lys Gly Ile Asp Phe Lys Glu Asp Gly Asn Ile Leu Gly His Lys Leu
    130                 135                 140
Glu Tyr Asn Tyr Asn Ser His Lys Xaa Val Tyr Ile Thr Ala Asp Lys
145                 150                 155                 160
Gln Lys Asn Gly Ile Lys Ala Asn Phe Lys Ile Arg His Asn Ile Glu
                165                 170                 175
Asp Gly Ser Val Gln Leu Ala Asp His Tyr Gln Gln Asn Thr Pro Ile
            180                 185                 190
Gly Asp Gly Pro Val Leu Leu Pro Asp Asn His Tyr Leu Ser Thr Gln
        195                 200                 205
Ser Ala Leu Ser Lys Asp Pro Asn Glu Lys Arg Asp His Met Val Leu
    210                 215                 220
Leu Glu Phe Val Thr Ala Ala Gly Ile Thr His Gly Met Asp Glu Leu
225                 230                 235                 240
Tyr Lys Glu Leu His His His His His
                245                 250
```

US 8,658,394 B2

METHODS, CELLS AND SYSTEMS FOR INCORPORATING NON-CANONICAL AMINO ACIDS INTO PROTEINS

STATEMENT REGARDING FEDERALLY SPONSORED RESEARCH

The present disclosure was not funded by federally sponsored research grants.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_32240_00003. The size of the text file is 26 KB, and the text file was created on May 24, 2012.

FIELD OF THE INVENTION

The present invention generally pertains to the field of protein chemistry. More particularly, but not by way of limitation, the present invention pertains to the genetic incorporation of non-canonical amino acids into proteins.

BACKGROUND OF THE INVENTION

With few exceptions, the genetic codes of all known organisms specify the same 20 canonical amino acid building blocks which sufficiently encode three dimensional protein structures. However, many proteins also require additional chemical groups beyond what the 20 building blocks can provide to carry out their native functions. Accordingly, approaches to synthesize proteins with defined posttranslational modifications have been developed for both research and therapeutic purposes. One such method is to genetically incorporate non-canonical amino acids (NAAs) directly into proteins during translation in live cells. However, such methods are limited in terms of efficiency, especially when multiple NAAs must be genetically incorporated into a protein. Accordingly, there is currently a need to develop more efficient methods, cells and systems for genetically incorporating non-canonical amino acids into proteins.

BRIEF SUMMARY OF THE INVENTION

In some embodiments, the present disclosure pertains to methods for incorporating a non-canonical amino acid into a protein during a translation of the protein in bacterial cells and/or in vitro translation systems (e.g., cell-free extract systems). Such methods generally utilize bacterial cells and/or in vitro translation systems that comprise: (1) a modified ribosome with a truncated L11 protein (L11-truncated ribosome); (2) a nucleotide sequence that encodes the protein; and (3) a suppressor transfer RNA that is acylated with the non-canonical amino acid (NAA-acylated suppressor transfer RNA). In such embodiments, the protein-encoding nucleotide sequence also includes an introduced stop codon at a site where the incorporation of the non-canonical amino acid into the protein is desired. In addition, the anti-codon of the NAA-acylated suppressor transfer RNA recognizes the introduced stop codon in the nucleotide sequence. Accordingly, during the translation of a transcript of the nucleotide sequence by the L11-truncated ribosome, the NAA-acylated suppressor transfer RNA incorporates the non-canonical amino acid into the translated protein at the desired site.

In more specific embodiments, the methods, bacterial cells and in vitro translation systems of the present disclosure can be used to incorporate a plurality of non-canonical amino acids into a protein. In such embodiments, the protein-encoding nucleotide sequences comprise a plurality of introduced stop codons at sites where the incorporation of the plurality of non-canonical amino acids into the protein is desired. In such embodiments, the anti-codon of the NAA-acylated suppressor transfer RNA recognizes the introduced stop codons.

In further embodiments, the methods, bacterial cells and in vitro translation systems of the present disclosure pertain to the incorporation of a plurality of distinct non-canonical amino acids into a protein. In such embodiments, a plurality of suppressor transfer RNAs are also provided that are each acylated with a distinct non-canonical amino acid. In addition, the anti-codon of each of the suppressor transfer RNAs in these embodiments recognizes one or more of the introduced stop codons in the nucleotide sequence.

In further embodiments, the present disclosure pertains to isolated bacterial cells for incorporating one or more non-canonical amino acids into a protein by the above-described methods. In additional embodiments, the present disclosure pertains to methods of incorporating one or more non-canonical amino acids into a protein during an in vitro translation of the protein. In additional embodiments, the present disclosure pertains to in vitro translation systems, such as cell-free extract systems, for incorporating one or more non-canonical amino acids into a protein by the above-described methods.

BRIEF DESCRIPTION OF THE FIGURES

For a more complete understanding of the present disclosure, and the advantages thereof, reference is now made to the following descriptions to be taken in conjunction with the accompanying Figures describing specific embodiments of the disclosure, wherein;

FIG. 4A illustrates Tandem MS spectrum of LEYNYNSHK*VYITADK from GFP-AcK. Similar spectra were obtained from GFP-2AcK and GFP-3AcK. K* is at position 149. Similarly, FIG. 4B illustrates Tandem MS spectrum of DNHYLSTK*SALSK from GFP-2AcK. Almost identical spectra were obtained from GFP-3AcK. K* is at position 204. FIG. 4C illustrates Tandem MS spectrum of DHYQK*NTPIG from GFP-3AcK. K* is at position 184. In all three panels, K* denotes AcK.

DETAILED DESCRIPTION OF EXEMPLARY EMBODIMENTS

Figure 1:
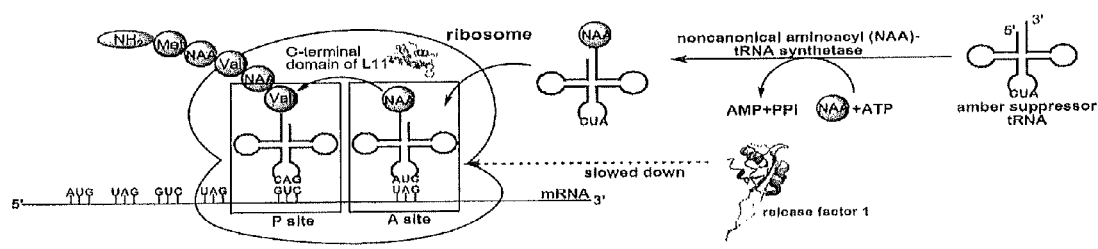
FIG. 1 illustrates the general steps involved in the incorporation of one or more non-canonical amino acids into a protein during a translation of the protein, in accordance with some embodiments of the present disclosure.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

The following definitions and explanations are meant and intended to be controlling in any future construction unless clearly and unambiguously modified in the Description or Examples below or when application of the meaning renders any construction meaningless or essentially meaningless. In cases where the construction of the term would render it meaningless or essentially meaningless, the definition should be taken from Webster's Dictionary, $3^{rd}$ Edition.

With few exceptions, the genetic codes of all known organisms specify the same 20 canonical amino acid building blocks which sufficiently encode three dimensional protein structures. However, it is clear that many proteins also require additional chemical groups beyond what the 20 building blocks can provide to carry out their native functions.[1, 2] Many of these groups are installed into proteins through covalent posttranslational modifications of amino acid side chains, including phosphorylation, sulfation, glycosylation, methylation, acetylation, hydroxylation, ubiquitylation, etc. These modifications, to a great extent, expand the amino acid inventory by assimilating noncanonical amino acids and grant proteins expanded opportunities for catalysis, initiation and termination of signal transduction, integration of information at many metabolic intersections, and alteration of cellular locations. The diversity of distinct covalent modifications greatly exceeds the number of proteins predicted by DNA coding capacities, leading to proteomes in higher organisms several orders of magnitude more complex than the encoding genomes and therefore adding a great complexity to the functional investigation of a lot of proteins.[1]

One major challenge in studying posttranslationally modified proteins is that they are typically produced as a mixture of different forms, making it difficult to purify uniquely modified forms from their natural sources. For this reason, a variety of approaches have been developed to synthesize proteins with defined posttranslational modifications, one of which is to genetically incorporate NAAs directly into proteins during translation in live cells. For instance, a general method for genetic NAA incorporation was developed by Schultz et al.[3-5] This method relies on the read-through of an in-frame amber (UAG) stop codon in mRNA by an amber suppressor transfer RNA specifically acylated with a NAA by an evolved aminoacyl-transfer RNA synthetase. Using this approach, more than thirty NAAs have been incorporated into proteins in bacteria, yeast or mammalian cells.[3,6,7] Three of these NAAs, O-GlcNac-L-serine,[8] O-sulfo-L-tyrosine,[9,10] and $N^\epsilon$-acetyl-L-lysine (AcK),[11] occur naturally in posttranslationally modified proteins. With the current accelerating rate of adding different NAAs into the repertoire of amino acid building blocks, the genetic incorporation of other NAAs with naturally existing modifications is anticipated.

Although the genetic NAA incorporation approach has opened a new avenue for functional studies of posttranslationally modified proteins, it does have its intrinsic limitation. Since the method mainly relies on the suppression of an amber stop codon, it has to compete with the release factor-1 (RF1)-mediated translation termination, which stops protein translation at the amber codon and generates truncated proteins.

Accordingly, the suppression efficiency for a single amber codon is generally limited to 10-20%. Furthermore, as the number of amber codons in a gene increases, the efficiency of NAA incorporation decreases multiplicatively. This creates a huge difficulty in the expression of proteins with multiple modified amino acids, which are abundant in nature. For example, seven acetylation sites have been discovered in histone 3.[12] Different acetylation patterns at these sites regulate cellular processes ranging from transcription activation to DNA repair.

Therefore, a modified genetic NAA incorporation approach that allows more efficient synthesis of proteins with multiple modifications is desired. Chin et al recently developed a system that used an evolved orthogonal ribosome (ribo-X) to improve amber suppression efficiency and achieved the incorporation of two NAAs into one protein.[13] As demonstrated herein, Applicants have developed a simpler and more efficient method for the genetic incorporation of NAAs into proteins.

As illustrated in FIG. 1, some embodiments of the present disclosure provide methods for incorporating one or more non-canonical amino acids into a protein. In some embodiments, the protein is encoded by a nucleotide sequence that has one or more introduced stop codons at sites where the incorporation of non-canonical amino acids into the protein is desired. In some embodiments, the nucleotide sequence is introduced into bacterial cells that contain ribosomes with truncated L11 proteins (i.e., L11-truncated ribosomes or modified ribosomes) and suppressor transfer RNAs that are acylated with non-canonical amino acids (NAA-acylated suppressor transfer RNAs). Desirably, the anti-codons in the NAA-acylated suppressor transfer RNAs recognize the introduced stop codons in the nucleotide sequence. Accordingly, during the translation of the nucleotide sequence transcript in the bacterial cells, the NAA-acylated suppressor transfer RNAs can incorporate the non-canonical amino acids into the desired sites in the protein. As discussed in more detail below, the L11-truncated ribosomes facilitate the efficiency of the translation process.

As also discussed in more detail below, the methods of the present disclosure can have numerous embodiments. For instance, in some embodiments, the methods of the present disclosure may be used to incorporate a single non-canonical amino acid into a protein during the translation of the protein in bacterial cells. In such embodiments, the methods of the present disclosure may utilize a nucleotide sequence that encodes the protein with a single introduced stop codon at the site where the incorporation of the non-canonical amino acid into the protein is desired. In such embodiments, the methods of the present disclosure also utilize one or more NAA-acylated suppressor transfer RNAs with anti-codons that recognize the introduced stop codon in the nucleotide sequence.

In other embodiments, the methods of the present disclosure may be used to incorporate multiple non-canonical amino acids into a protein. In such embodiments, the methods of the present disclosure may utilize a nucleotide sequence that encodes the protein with multiple introduced stop codons at the sites where the incorporation of the non-canonical amino acids into the protein is desired. In such embodiments, the methods of the present disclosure may also utilize one or more NAA-acylated suppressor transfer RNAs with anti-codons that recognize the introduced stop codons in the nucleotide sequence. For instance, and as discussed in more detail below, this method has been successfully used to incorporate three $N^\epsilon$-acetyl-L-lysines into a green fluorescent protein ($GFP_{UV}$) protein in E. coli.

In some embodiments, the non-canonical amino acids to be incorporated into a protein may be the same amino acids. In other embodiments, the non-canonical amino acids may be different. Accordingly, the methods of the present disclosure may also utilize multiple NAA-acylated suppressor transfer RNAs that are acylated with different non-canonical amino acids.

Furthermore, numerous proteins may be modified by the methods of the present disclosure. In addition, the methods of the present disclosure may utilize various protein-encoding nucleotide sequences, introduced stop codons, NAA-acylated suppressor transfer RNAs, L11-truncated ribosomes, and bacterial cells. In further embodiments, the methods of the present disclosure may occur in vitro rather than in bacterial cells, such as through the use of an in vitro translation system or kit. Reference will now be made to the more detailed aspects of the present disclosure for illustrative purposes only.

Non-Canonical Amino Acids

Non-canonical amino acids in the present disclosure generally refer to amino acids that are distinguishable from the 20 canonical amino acids that constitute the building blocks of proteins. For instance, in some embodiments, non-canonical amino acids may be posttranslationally modified versions of canonical amino acids. Such posttranslational modifications can include, without limitation, phosphorylation, sulfation, glycosylation, methylation, acetylation, hydroxylation, and ubiquitylation. Specific examples of posttranslationally modified non-canonical amino acids include, without limitation, O-sulfo-L-tyrosine, O-phospho-L-tyrosine, m-nitro-L-tyrosine, $N^\epsilon$-methyl-L-lysine, $N^\epsilon$, $N^\epsilon$-dimethyl-lysine, $N^\epsilon$, $N^\epsilon$, $N^\epsilon$-trimethyl-lysine, $N^\epsilon$-succinyl-L-lysine, $N^\epsilon$-malonyl-L-lysine and $N^\epsilon$-acetyl-L-lysine (AcK).

In other embodiments, non-canonical amino acids may be any amino acids that can be incorporated into proteins by nonsense suppression. Specific examples include, without limitation, p-azido-L-phenylalanine, p-benzoyl-L-phenylalanine, p-propargyloxy-L-phenylalanine, p-iodo-L-phenyalanine, p-acetyl-L-phenylalanine, and p-nitro-L-phenylalanine, p-(1',3'-dioxobutyl)-L-phenylalanine, Se-phenyl-L-selenocysteine, 4'-[3-(trifluoromethyl)-3H-diazirin-3-yl]-L-phenylalanine, O-nitrobenzyl-L-tyrosine, p-(phenylazo)-L-phenylalanine, p-carboxymethyl-L-phenylalanine, (S)-2-amino-4-(7-hydroxy-2-oxo-2H-chromen-4-yl)butanoic acid, p-bromo-L-phenylalanine, O-methyl-L-tyrosine, p-cyano-L-phenylalanine, m-cyano-L-phenylalanine, 3,4-dihydroxy-L-phenylalanine, 3-amino-L-tyrosine, p-amino-L-phenylalanine, (S)-3-(2,2'-bipyridin-5-yl)-2-aminopropanoic acid, 3-(8-hydroxyquinolin-3-yl)-L-alanine, $N^\epsilon$-(t-butylcarbamoyl)-L-lysine, $N^\epsilon$-propargyloxycarbonyl-L-lysine, $N^\epsilon$-(2-azidoethyloxycarbonyl)-L-lysine, $N^\epsilon$-(o-nitrobenzyloxycarbonyl)-L-lysine, $N^\epsilon$-(o-nitrobenzyloxycarbonyl)-$N^\epsilon$-methyl-L-lysine, $N^\epsilon$-(benzyloxycarbonyl)-L-lysine, $N^\epsilon$-(benzyloxycarbonyl)-$N^\epsilon$-methyl-L-lysine, $N^\epsilon$-(L-cysteinyl)-L-lysine, $N^\epsilon$-(D-cysteinyl)-L-lysine, and L-2-amino-8-oxononanic acid.

A person of ordinary skill in the art can also envision other non-canonical amino acids that may be used with various embodiments of the present disclosure. For instance, in some embodiments, the non-canonical amino acids may constitute small molecules. In more specific embodiments, the small molecules may be structurally distinct from the chemical structures of the 20 canonical amino acids.

Proteins

The non-canonical amino acids of the present disclosure may be incorporated into numerous proteins. For instance, in some embodiments, the protein may be a recombinant protein. Such recombinant proteins may be derived from various organisms. For instance, in some embodiments, the recombinant protein may be a human protein. In other embodiments, the recombinant protein may be a mouse protein or a bacterial protein.

In additional embodiments, the non-canonical amino acids of the present disclosure may be incorporated into native proteins of an organism. For instance, in some embodiments, one or more non-canonical amino acids may be incorporated into a native protein of a bacterium, such as E, coli.

Nucleotide Sequences

The modified proteins of the present disclosure may be encoded by numerous nucleotide sequences. In some embodiments, the nucleotide sequences may be part of an expression vector, such as a plasmid. In such embodiments, the expression vector containing the nucleotide sequence may be introduced into a bacterial cell for expression (i.e., transcription followed by translation). As discussed in more detail below, the expression vector containing the nucleotide sequence may also be used in an in vitro translation system.

In other embodiments, the protein-encoding nucleotide sequences of the present disclosure may be genetically incorporated into a genome of an organism, such as the bacterial genome. Various methods well known by persons of ordinary skill in the art may be used to implement such genetic incorporation. For instance, in some embodiments, a protein-encoding nucleotide sequence may be incorporated into a bacterial genome by transduction.

Applicants also note that, in other embodiments, the protein to be modified may be encoded by a native gene in an organism. Accordingly, in such embodiments, the genetic incorporation of non-canonical amino acids into a protein can occur without the need to utilize an exogenous nucleotide sequence of that protein.

Stop Codons in Nucleotide Sequences

Protein-encoding nucleotide sequences of the present disclosure preferably contain one or more stop codons at sites where the incorporation of non-canonical amino acids into the protein is desired. In some embodiments, the one or more stop codons may be amber stop codons (i.e., 5'-UAG-3' in RNA or 5'-TAG-3' in DNA). In other embodiments, the one or more stop codons may be ochre stop codons (i.e., 5'-UAA-3' in RNA or 5'-TAA-3' in DNA). In additional embodiments, the stop codons may be amber and ochre stop codons.

In some embodiments, the stop codons may be naturally occurring stop codons in an organism. In other embodiments, the stop codons may be introduced to the nucleotide sequence by various methods, such as site-directed mutagenesis.

Expression of the Nucleotide Sequence

Protein-encoding nucleotide sequences of the present disclosure can be expressed by many methods known to persons of ordinary skill in the art. For instance, in some embodiments, the nucleotide sequence may be inserted into an IPTG-inducible expression vector (e.g., a plasmid, such as pET-Duet-1). The expression vector may then be transformed into bacterial cells that contain NAA-acylated suppressor transfer RNAs and L11-truncated ribosomes. Thereafter, the transformed bacterial cells may be treated with IPTG to induce the transcription of the nucleotide sequence. Next, the transcript may be translated by the L-11 truncated ribosome and the NAA-acylated suppressor transfer RNAs to lead to the incorporation of the non-canonical amino acids into the desired sites in the translated protein.

NAA-acylated Suppressor Transfer RNAs

The stop codons at sites where the incorporation of non-canonical amino acids into a protein is desired are preferably recognized by the anti-codons of NAA-acylated suppressor transfer RNAs. As illustrated in FIG. 1, NAA-acylated suppressor transfer RNAs may be provided by acylating a transfer RNA with a non-canonical amino acid. This may be performed by an aminoacyl-transfer RNA synthetase. For instance, in some embodiments, the methods of the present disclosure may utilize mutant aminoacyl-transfer RNA synthetases (AcKRSs) that are specific for a desired non-canonical amino acid, such as acetylated lysine (AcK). By way of background, many AcKRSs have been evolved from Methanosarcina barkeri pyrrolysyl-transfer RNA synthetase. Together with M. barkeri pylT, the cognate amber suppressor transfer RNA of pyrrolysyl-transfer RNA synthetase, these mutant variants have been used to incorporate AcK into proteins in both E. coli and mammalian cells.[11,19] Other methods of providing NAA-acylated suppressor transfer RNAs can also be envisioned by a person of ordinary skill in the art.

L-11-truncated Ribosomes

L-11 truncated ribosomes (or modified ribosomes) generally refer to ribosomes that comprise a truncated L11 protein. By way, of background, the L11 protein refers to large ribosomal subunit protein L11 in E. coli. L11 is a highly conserved small ribosomal protein that is associated with 23S rRNA. L11 contains two domains, N- and C-terminal domains linked together by a small peptide hinge. It has been suggested from biochemical, cryoelectron micrographic, and X-ray crystallographic studies that L11 plays an important role in the RF1-mediated peptide release.[14-18]

Knockout of the N-terminal domain of L11 (L11N) from E. coli led to normal cell growth but with a high amber suppression rate.[14] However, E. coli lacking the entire L11 protein was thermosensitive and showed a drastically decreased cell growth rate.[14] Without being bound by theory, these studies indicate that the C-terminal domain of L11 (L11C) alone efficiently binds 23S rRNA to maintain regular protein translation efficiency but with a high amber suppression rate. The in vitro analysis also proved 4-6 folds reduction in the RF1-mediated termination efficiency when the ribosome did not contain L11N.[18]

Based on the above-mentioned observations, Applicants hypothesized that the over-expression of L11C inside E. coli would efficiently replace L11 in a ribosome, consequently decrease the RF1-mediated translation termination at stop codons (e.g., amber codons), and increase stop codon suppression efficiency. Applicants also envisioned that this enhanced suppression level may allow the incorporation of multiple NAAs into a protein.

Applicants envision the use of numerous L-11 truncated ribosomes with the embodiments of the present disclosure. For instance, in some embodiments, the L11 truncation may be at the N-terminus of the protein. In more specific embodiments, the truncation may be at the first 72 amino acids of the N-terminus of the L-11 protein.

L-11 truncated ribosomes may also be produced by various methods. For instance, in some embodiments, the L-11 truncated ribosome may be provided by over-expressing the truncated L11 protein in bacterial cells. In some embodiments, such over-expression can occur by the introduction of a plasmid that contains the encoding sequence for the truncated L11 protein into the bacterial cells. In other embodiments, the L-11 truncated ribosome may be provided by genetically incorporating the nucleotide sequence that encodes the truncated L-11 protein into the bacterial genome. In additional embodiments, the L-11 truncated ribosome may be provided by genetically knocking out a part of the N-terminal domain of the L-11 protein from the bacterial genome. Other methods of providing L-11 truncated ribosomes can also be envisioned by a person of ordinary skill in the art.

Bacterial Cells

The methods of the present disclosure can occur in numerous bacterial cells. For instance, in some embodiments, the methods of the present disclosure can occur in E. coli cells, such as BL21 cells. Other bacterial cells known by persons of ordinary skill in the art can also be used to carry out the methods of the present disclosure.

Other aspects of the present disclosure also pertain to an isolated bacterial cell for synthesizing a protein with one or more non-canonical amino acids. Such bacterial cells generally include (1) an L11-truncated ribosome; (2) a nucleotide sequence that encodes the protein of interest and contains one or more stop codons at sites where the incorporation of non-canonical amino acids into the protein is desired; and (3) one or more NAA-acylated suppressor transfer RNAs with anti-codons that recognize the stop codons in the nucleotide sequence. Accordingly, the translation of the transcript of the nucleotide sequence in such bacterial cells by the use of the L11-truncated ribosome and the NAA-acylated suppressor transfer RNAs results in the incorporation of non-canonical amino acids into the translated protein.

A person of ordinary skill in the art can also envision that the methods of the present disclosure may occur outside bacterial cells. For instance, in some embodiments, the methods of the present disclosure may occur in yeast cells, mammalian cells, or other eukaryotic cells. Furthermore, and as discussed in more detail below, a person of ordinary skill in the art will recognize that the methods of the present disclosure can occur in vitro, such as in cell-free extract systems.

In Vitro Translation Methods and Systems

In some embodiments, the present disclosure can pertain to methods of incorporating one or more non-canonical amino acids into a protein during an in vitro translation of the protein. Such methods generally utilize an in vitro translation system (e.g., cell-free extract system) that includes: (1) an L11-truncated ribosome; (2) a nucleotide sequence that encodes the protein of interest and contains one or more stop codons at sites where the incorporation of non-canonical amino acids into the protein is desired; and (3) one or more NAA-acylated suppressor transfer RNAs with anti-codons that recognize the stop codons in the nucleotide sequence. The in vitro translation systems of the present disclosure can also contain additional components that are necessary to implement protein translation. In some embodiments, the in vitro translation systems of the present disclosure are cell-free extract systems, such as bacterial cell lysates. In some embodiments, the bacterial cell lysates may be derived from E. coli.

In operation, in vitro translation systems of the present disclosure may be used to transcribe the above-mentioned nucleotide sequence. The transcript may be then be translated by the use of the L11-truncated ribosome and the NAA-acylated suppressor transfer RNAs to result in the incorporation of non-canonical amino acids into the translated protein.

Applications

A person of ordinary skill in the art will recognize that the methods, cells and systems of the present disclosure may be used in various settings and for numerous purposes. For instance, in some embodiments, the methods, cells and systems of the present disclosure may be used to produce post-translationally modified proteins for therapeutic purposes. In other embodiments, the methods, cells, and systems of the present disclosure may be used to produce such modified proteins for research purposes.

From the above disclosure, a person of ordinary skill in the art will also recognize that the present invention has numerous other embodiments and applications. Reference will now be made to more specific embodiments of the present disclosure and experimental results that provide support for such embodiments. However, Applicants note that the disclosure below is for exemplary purposes only and is not intended to limit the scope of the claimed invention in any way.

To demonstrate the efficacy of the above-mentioned methods, cells, and systems, Applicants chose to incorporate multiple copies of AcK into one protein in E. coli. For that purpose a plasmid pAcKRS-pylT-GFP1Amber bearing the genes encoding an AcKRS variant with mutations D76G/L266V/L270I/Y271F/L273A/C313F, pylT and $GFP_{UV}$ with an amber mutation at position 149 were constructed from the pETduet-1 vector (Stratagene Inc.).

Figure 2:
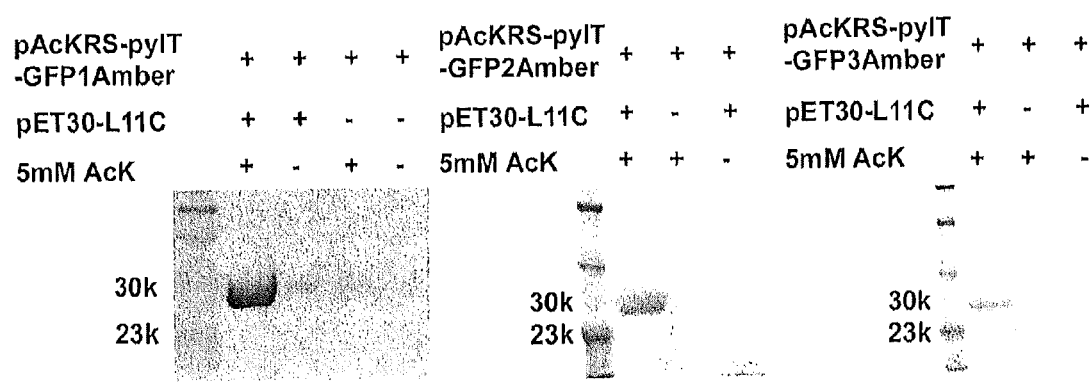
FIG. 2 illustrates the incorporation of non-canonical amino acids into $GFP_{UV}$, in accordance with some embodiments of the present disclosure.

In this plasmid, AcKRS and $GFP_{UV}$ are both under the control of IPTG-inducible T7 promoters and pylT is flanked by the lpp promoter and the rrnC terminator. The transformation of this plasmid into BL21 cells and subsequent growth in LB medium supplemented with 5 mM AcK and 500 μM IPTG afforded full-length $GFP_{UV}$ with a yield of 0.8 mg/L. As shown in FIG. 2A, a trace amount of full-length $GFP_{UV}$ was expressed when AcK was absent in LB media.

Applicants then tested whether over-expression of L11C could improve amber suppression rate. Accordingly, L11C (residues 72-144 of L11) was cloned into the pET30a vector (Stratagene Inc.) to afford pET-L11C, in which L11C is under the control of an IPTG-inducible T7 promoter. As also shown in FIG. 2A, transformation of BL21 cells with both pAcKRS-pylT-GFP1Amber and pET-L11C and subsequent growth in LB medium with the addition of 5 mM AcK and 500 μM IPTG led to full-length $GFP_{UV}$ production with a yield of 3.5 mg/L. This yield was four times higher than that from cells transformed only with pAcKRS-pylT-GFP1Amber.

Figure 3:
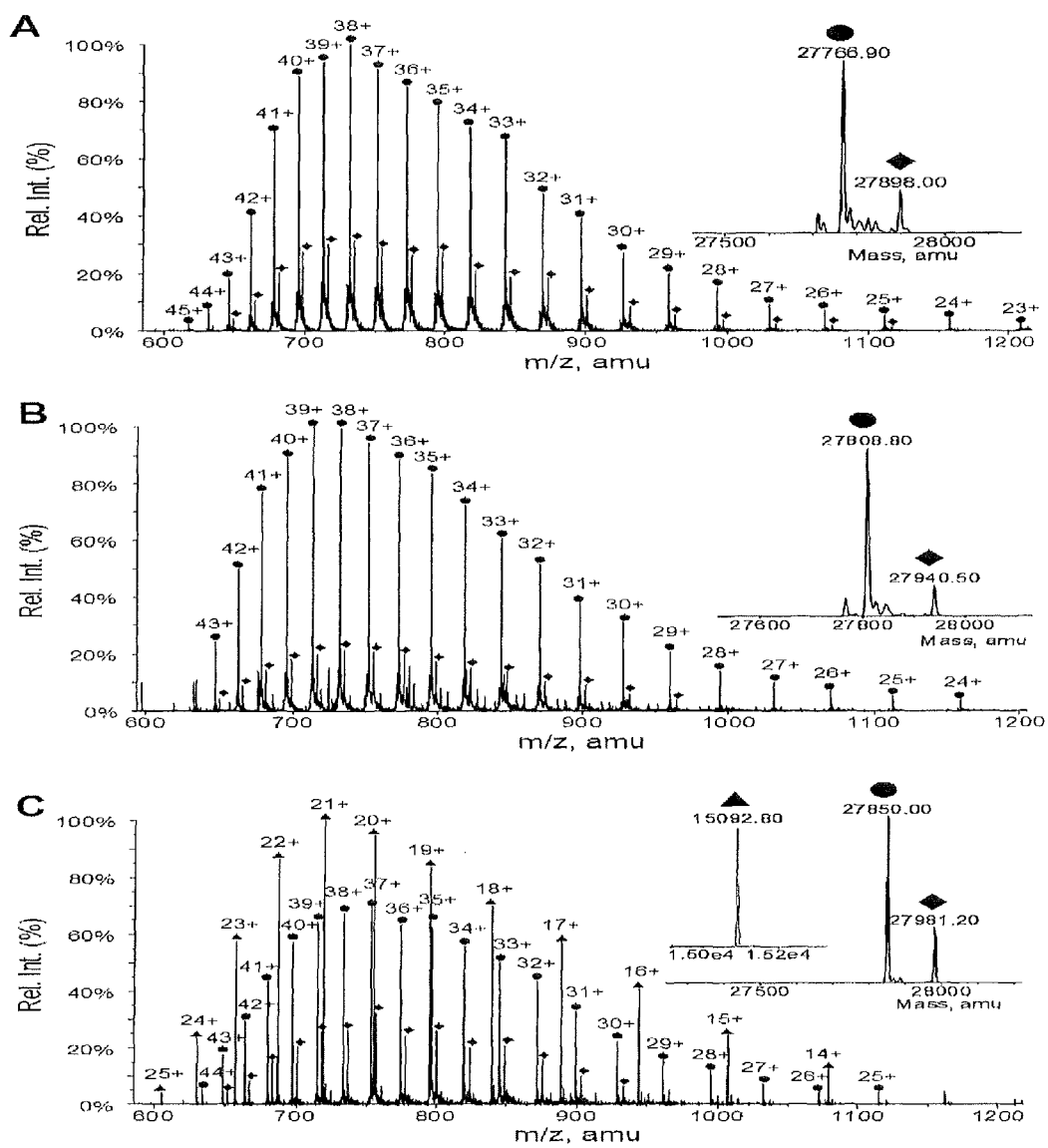
FIG. 3 illustrates ESI-TOF MS spectra of GFP-AcK (FIG. 3A), GFP-2AcK (FIG. 3B), and GFP-3AcK (FIG. 3C) expressed in cells containing over-expressed L11C. The inlets are de-convoluted MS spectra. Full-length proteins with and without N-terminal methionine are denoted by ◆ and ●, respectively.

As shown in FIG. 3A, the electrospray ionization time-of-flight mass spectrometry (ESI-TOF MS) of full-length $GFP_{UV}$ purified from cells transformed with two plasmids revealed two intense peaks corresponding to the mutated $GFP_{UV}$ (GFP-AcK), which contains AcK at position 149, with and without the N-terminal methionine, respectively. In addition, as shown in FIG. 4A, the tandem mass spectrum of the tryptic AcK-containing fragment of LEYNYNSHK*VYITADK (K* denotes AcK) validated the incorporation of AcK at position 149. In addition, the presence of K* containing ions ($y_8$ to $y_{15}$ and $b_9$ to $b_{15}$) all had the expected mass.

To test whether L11C over-expression improves the basal level of amber suppression, the BL21 cells transformed with both pAcKRS-pylT-GFP1Amber and pET-L11C were grown in LB medium supplemented only with 500 μM IPTG. In the absence of AcK, full-length $GFP_{UV}$ was expressed with a yield of 0.2 mg/L, indicating a significant basal amber suppression improvement. Since the evolved AcKRS still showed low activity toward natural amino acids in LB medium,[11, 19] this basal amber suppression improvement may represent the improved ability of AcKRS to incorporate natural amino acids into proteins. ESI-TOF MS of the purified full-length $GFP_{UV}$ expressed in this condition revealed five peaks, of which one (27766 Da) matched the mass of GFP-AcK without N-terminal methionine but the other four (27710 Da, 27725 Da, 27782 Da, and 27842 Da) were not identified in ESI-TOF MS of GFP-AcK purified from the same cells growing in the presence of AcK. These results indicate that the presence of AcK efficiently inhibits the incorporation of other amino acids, assuring the high fidelity of AcK incorporation.

The above-results demonstrated that the over-expression of L11C indeed enhances amber suppression efficiency and maintains high NAA incorporation fidelity as well. Next, Applicants tested the feasibility to use the L11C over-expression to incorporate two AcKs into one protein in E. coli. Accordingly, an additional amber mutation was introduced into position 204 of the $GFP_{UV}$ gene in pAcKRS-pylT-GFP1Amber to afford pAcKRS-pylT-GFP2Amber. Together with or without pET-L11C, the modified plasmid was transformed into BL21 cells. As shown in FIG. 2B, subsequent cell growth in LB medium supplemented with 5 mM AcK and 500 μM IPTG led to the production of $GFP_{UV}$ incorporated with AcKs at positions 149 and 204 (GFP-2AcK) in cells that were transformed with two plasmids. The expression yield was ~0.2 mg/L. In contrast, and as also shown in FIG. 2B, only trace amounts of GFP-2AcK was expressed in the cells that were transformed with only pAcKRS-pylT-GFP2Amber.

As shown in FIG. 3B, the ESI-TOF MS analysis of the purified GFP-2AcK from cells transformed with two plasmids confirmed the expected incorporation. Furthermore, as shown in FIGS. 4A and 4B, the incorporation of AcKs at positions 149 and 204 was also independently confirmed by tandem mass spectral analysis of tryptic and endoproteinase Asp-N-digested AcK-containing fragments.

Figure 4:
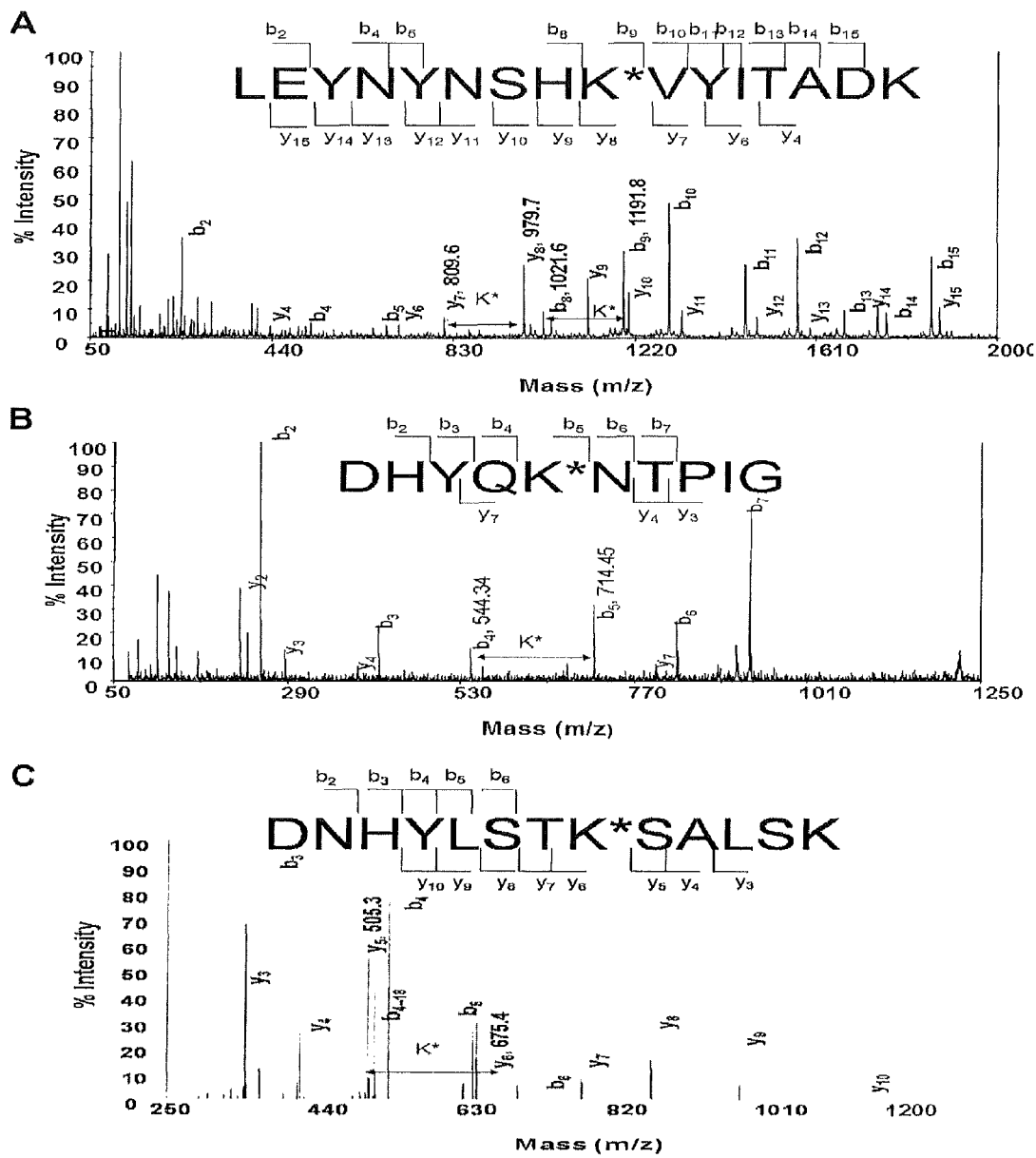
FIG. 4 illustrates Annotated tandem MS spectra of proteolytic $GFP_{UV}$ fragments. In particular.

To further evaluate the efficiency of the systems, cells and methods of the present disclosure, Applicants incorporated three AcKs into $GFP_{UV}$ in E. coil. One more amber mutation was installed at position 184 of the $GFP_{UV}$ gene in the plasmid pAcKRS-pylT-GFP2Amber to afford pAcKRS-pylT-GFP3Amben Together with pET-L11C, this plasmid was used to express $GFP_{UV}$ incorporated with three copies of AcK (GFP-3AcK) in E. coli, following the exactly same procedures used in GFP-2AcK expression, GFP-3AcK was expressed in cells transformed with both pAcKRS-pylT-GFP3Amber and pET-L11C with a final yield of ~0.1 mg/L. No GFP-3AcK expression was detected in cells transformed only with pAcKRS-pylT-GFP3Amber. ESI-TOF MS of purified full-length GFP-3AcK and tandem MS analysis of proteolytic AcK-containing peptide fragments confirmed that three AcKs were indeed incorporated into positions 149, 184, and 204 (FIG. 3C and FIG. 4).

Table 1 below summarizes the above-mentioned experimental results,

TABLE 1

| | | | | |
|---|---|---|---|---|
| $GFP_{UV}$ expression yields and MS characterization. | | | | |
| Protein[a] | L11C co-expression | Concentration (mg/L) | Calculated Mass (Da) | Actual Mass (Da) |
| GFP-AcK | + | 3.5 | 27766[b] 27897[c] | 27767 27898 |
| | − | 0.8 | | |
| GFP-2AcK | + | 0.2 | 27808[b] 27939[c] | 27809 27940 |
| | − | trace | | |
| GFP-2AcK' | + | 1.4 | 28082[c] | 28004 |
| | − | trace | | |
| GFP-3AcK | + | 0.1 | 27850[b] 27981[c] | 27850 27981 |
| | − | N.D. | | |

[a]Proteins were expressed in the presence of 5 mM AcK and 500 μM IPTG.
[b]Molecular mass of full-length protein without N-terminal methionine.
[c]Molecular mass of full-length protein.

Although Applicants have not yet attempted to incorporate more than three AcKs into one protein, Applicants envision that such higher levels of incorporation are feasible, especially since the $GFP_{UV}$ expression level only decreased 50% from two amber mutations to three.

Without being bound by theory, the drastic decline of GFP$_{UV}$ expression level from one amber mutation to two might be due to protein folding difficulty when AcK is introduced at position 204. Applicants envision that the choice of the position to introduce a NAA into a protein usually affects the protein expression yield to a great extent. This phenomenon has been frequently observed during expression of proteins incorporated with different NAAs.[20] Nonetheless, the protein expression yield of 0.1 mg/L can be sufficient for many research and therapeutic purposes.

To determine whether the above-mentioned expression level decrease is due to the choice of the position at which AcK is introduced, Applicants expressed GFP$_{UV}$ incorporated with two AcKs at positions 2 and 149 (GFP-2AcK'). An additional amber mutation was introduced into position 2 of the GFP$_{UV}$ gene in pAcKRS-pylT-GFP1Amber to afford pAcKRS-pylT-GFP2Amber' in which an alanine insertion was also introduced into the GFP$_{UV}$ gene between the start codon ATG and the amber codon at position 2 to relieve possible difficulty of protein translation when ribosome immediately meets a stop codon right after a start codon. Together with or without pET-L11C, the modified plasmid was used to transform BL21 cells. Subsequent cell growth in LB medium supplemented with 5 mM AcK and 500 µM IPTG led to the production of GFP-2AcK' with an expression yield of ~1.4 mg/L that is seven times higher than the GFP-2AcK expression under the same condition. Cells transformed with only pAcKRS-pylT-GFP2Amber' yielded non-detectable GFP-2AcK'. The ESI-TOF MS analysis of the purified GFP-2AcK' confirmed the expected incorporation (See Table 1-calculated mass: 28082 Da; detected mass: 28084 Da). This demonstrates that the low protein expression level of GFP-2AcK is a consequence of choosing position 204 to introduce the second AcK that may affect protein folding.

EXAMPLES

Additional details about the experimental aspects of the above-described studies are discussed in the subsections below.

Example 1

Construction of Plasmids

The construction of pAcKRS-pylT-GFP1Amber, pET-L11C, pAcKRS-pylT-GFP2Amber, and pAcKRS-pylT-GFP3Amber all followed standard cloning and QuikChange site-directed mutagenesis procedures using Platinum Pfx (Invitrogen) and PfuTurbo (Stratagene) DNA polymerases. Sequences of all plasmids constructed were verified by sequencing. All oligonucleotide primers were purchased from Integrated DNA Technologies, Inc.

Construction of pBK-AcKRS-pylT

M. barberi pyrrolysyl-transfer RNA systhetase (MbPylRS) was amplified from M. barkeri genomic DNA purchased from ATCC by polymerase chain reaction (PCR) using two primers:

```
GAGGAATCCCATATGGATAAAAAACCATTAG;
and

CGTTTGAAACTGCAGTTACAGATTGGTTG.
```

AcKRS (L266V, L270I, Y271F, L274A, C313F and D76G) was subsequently synthesized by overlap extension PCR using MbPylRS as the template and eight oligodeoxynucleotide primers:

```
GAGGAATCCCATATGGATAAAAAACCATTAG;

AAATTATTGATATCCTCGCCCGAAACCCTACATCGTTTGC;

GATGTAGGGTTTCGGGCGAGGATATCAATAATTTTC;

GTTGAAAATAGTCGGGGCAACCATTGGCCTCAAGCAG;

GCCCCGACTATTTTCAACTATGCGCGAAAACTCGATAGG;

CCGAACCCATCTGAAAGAAGTTCACCATAG;

CTATGGTGAACTTCTTTCAGATGGGTTCGG;
and

CGTTTGAAACTGCAGTTACAGATTGGTTG).
```

Two restriction sites, Nde1 at 5' head and Pst1 at 3' tail, were designed into the synthesized AcKRS, which was subsequently digested by NdeI and PstI restriction enzymes and cloned into the same two sites in a pBK plasmid to afford pBK-AcKRS.

In pBK-AcKRS, AcKRS is under the control of a constitutive glnS promoter. The gene of pylT flanked by the lpp promoter at 5' end and the rrnC terminator at 3' end was constructed by using overlap extension PCR of six oligodeoxynecleotides:

```
CCCGGGATCCCCCATCAAAAAAATATTCTCAACAT;

TTACAAGTATTACACAAAGTTTTTTATGTTGAGAATATTTTTTTG;

ACTTTGTGTAATACTTGTAACGCTGAATCCGGAAACCTGATCATGTAGAT;

CTAACCCGGCTGAACGGATTTAGAGTCCATTCGATCTACATGATCA
GGTTT;

TCAGCCGGGTTAGATTCCCGGGGTTTCCGCCACTGCCCATCCTTAGCGAA;
and

GAACCCAGATCTTAAAAAAAATCCTTAGCTTTCGCTAAGGATG.
```

Two restriction sites, BamH1 at 5' end and Bgl11 at 3' end, were introduced in the synthesized DNA which was subsequently digested by these two enzymes and cloned into the BamH1 site in pBK-AcKRS to afford pBK-AcKRS-pylT. The use of pBK-AcKRS-pylT together with 5 mM AcK to suppress an amber codon at position 149 of GFP$_{UV}$ in BL21 cells was tested but did not give high amber suppression efficiency. Applicants then decided to put AcKRS under the control of a stronger promoter and constructed the plasmid pAcKRS-pylT-GFP1Amber.

Construction of pAcKRS-pylT-GFP1Amber

Plasmid pAcKRS-pylT-GFP1Amber encodes the AcKRS/pylT pair and GFP1Amber with one amber mutation at position 149. Both of AcKRS and GFP1Amber were under the control of the T7 promoters, AcKRS was amplified from pBK-AcKRS-pylT by two oligodeoxynucleotides:

```
GATATAACATGTCAGATAAAAAACCATTAGATG;
and

GTCGACCTGCAGTTACAGATTGGTTGAAATCCC.
```

The amplified DNA was digested by Pci1 end and Pst1 restriction enzymes and cloned into the Nco1 and Pst1 sites of pETduet-1, which was purchased from Stratagene Inc to afford pAcKRS.

GFP1Amber was amplified from pleiG-N149 (a gift from Dr. Peter G. Schultz) by two oligodeoxynucleotides:

```
GAAGGAGATATACATATGAGTAAAGGAGAAG;
and

GACTCGAGGGTACCTTAGTGATGGTGATGGTGATG.
```

The amplified DNA was digested by NdeI and KpnI, and then cloned into NdeI and KpnI restriction sites of pAcKRS to afford pAcKRS-GFP1Amber, pylT with the lpp promoter and the rrnC terminator was amplified from pBK-AcKRS-pylT by two oligodeoxynucleotides:

```
GCTAGATCTGGAAACCTGATGTAGATC;
and

GATACTAGTTGGCGGAAACCCCGGG.
```

The amplified DNA digested by SphI, and then cloned into the SphI site of pAcKRS-GFP1Amber to afford pAcKRS-pylT-GFP1Amber.

Construction of pAcKRS-pylT-GFP2Amber

Plasmid pAcKRS-pylT-GFP2Amber was derived from pAcKRS-pylT-GFP1Amber with an addition amber mutation at position 204. The mutagenesis was carried out by the standard QuikChange site-directed mutagenesis procedure using PfuTurbo DNA polymerase and two oligonucleotides:

```
CTTTCGAAAGGGCAGACTATGTCGACAGGTAATG;
and

CATTACCTGTCGACATAGTCTGCCCTTTCGAAAG.
```

Construction of pAcKRS-pylT-GFP3Amber

Plasmid pAcKRS-pylT-GFP3Amber was derived from pAcKRS-pylT-GFP2Amber with an additional amber mutation at position 184. The mutagenesis was carried out by the standard QuikChange site-directed mutagenesis procedure using PfuTurbo DNA polymerase and two oligonucleotides:

```
ATCGCCAATTGGAGTATTCTATTGATAATGGTCTGC;
and

GCAGACCATTATCAATAGAATACTCCAATTGGCGAT.
```

Construction of pET-L11C

Plasmid pET-L11C contains the gene of L11C whose transcription is under the control of T7 promoter. L11C gene was amplified from the genomic DNA of *E. coli* by standard PCR using two primers:

```
GGAGATATACATATGACCAAGACCCCGCCGGCA;
and

GTCGTCGGTACCTTAGTCCTCCACTACCAG.
```

The amplified DNA was digested by NdeI and KpnI restriction enzymes and cloned into NdeI and KpnI sites in pET30a (Stratagene Inc.) to afford pET-L11C.

Example 2

GFP$_{UV}$ Expression and Purification

To express different kinds of GFP$_{UV}$ variants, *E. coli* BL21 cells was transformed with pAcKRS-pylT-GFP1Amber, pAcKRS-pylT-GFP2Amber, or pAcKRS-pylT-GFP3Amber together with or without pET-L11C. The cells transformed with one plasmid were grown in LB media that contained 100 μg/mL ampicillin and induced with the addition of 500 μg/mL IPTG when OD$_{600}$ was 0.6. 5 mM AcK and 5 mM nicotinamide were subsequently added into the media 0.5 h after induction. The cells were then grown overnight or 10 h at 37 degree. The protein expression in cells transformed with two plasmids followed exactly same procedures except the addition of 25 μg/mL kanamycin into the media to force cells to maintain pET30-L11C. The GFP$_{UV}$ expression in cells transformed with either one or two plasmids at the absence of AcK also followed the same procedures. Cells were harvested by centrifugation (4500 r.p.m., 20 min, 4 degree) and re-suspended in 20 mL of lysis buffer (50 mM HEPES, pH 7.4, 500 mM NaCl, 10 mM DTT, 10% glycerol, 0.1% Triton X-100, 5 mM imidazole, and 1 μg/mL lysozyme). The resuspended cells were sonicated and the lysate was clarified by centrifugation (10200 r.p.m., 60 min, 4 degree). The supernatant was decanted and loaded to Ni-NTA superspeed agarose (Qiagen Inc.) column on FPLC. The column was washed by 5× bed volume of buffer A that contained 50 mM HEPES, pH 7.5, 300 mM NaCl, 5 mM imidazole and then eluted by running a gradient that changed from buffer A to buffer B in 10× bed volume. Buffer B contained 50 mM HEPES, pH 7.5, 300 mM NaCl, 250 mM imidazole. Proteins were concentrated by Amicon (Millipore, NMWL 10 KDa) and analyzed by 12% SDS-PAGE.

Example 3

Mass Spectrometry Analysis

LC-ESI-MS Analysis of Intact Protein

An Agilent (Santa Clara, Calif.) 1200 capillary HPLC system was interfaced to an API QSTAR Pulsar Hybrid QTOF mass spectrometer (Applied Biosystems/MDS Sciex, Framingham, Mass.) equipped with an electrospray ionization (ESI) source, Liquid chromatography (LC) separation was achieved using a Phenomenex Jupiter C4 microbore column (150×0.50 mm, 300 Å) (Torrance, Calif.) at flow rate of 10 μL min-1. The proteins were eluted using a gradient of (A) 0.1% formic acid versus (B) 0.1% formic acid in acetonitrile. The gradient timetable was as follows: 2% B for 5 min, 2-30% in 3 min, 30-60% in 44 min, 60-95% in 8 min, followed by holding the gradient at 95% for 5 min, for a total run time of 65 min. The MS data were acquired in positive ion mode (500-2000 Da) using spray voltage of +4900 V. BioAnalyst software (Applied Biosystems) was used for spectral de-convolution. A mass range of m/z 500-2000 was used for de-convolution and the output range was 10000-50000 Da using a step mass of 0.1 Da and a S/N threshold of 20.

Protein Digestion

GFP$_{UV}$ variants were dissolved in 25 mM Ammonia bicarbonate, and denatured at 90 degree for 15 min. Trypsin (Sigma) or Proteinase Asp-N (Roche) was dissolved in 0.01% TFA (pH 3). Trypsin or Proteinase Asp-N solution was added to the substrate protein solution (w/w=1:50), and incubated at 37 degree overnight.

Tandem-MS of Proteolytic Peptides

Peptides resulting from tryptic digests were mixed 1:1 (v/v) with matrix (5 mg mL$^{-1}$ α-cyano-4-hydroxycinnamic acid, 50% (v/v) acetonitrile, 10 mM ammonium dihydrogen phosphate, 1% TFA) and 1 μL of the resulting mixture was spotted onto a stainless steel target plate. Mass spectra and tandem MS spectra were collected using an Applied Biosystems 4800 Tof/Tof (Framingham, Mass.). Collision induced dissociation tandem MS spectra were acquired using air at the medium pressure setting and at 2 kV of collision energy. Tandem MS data was manually interpreted using the Data Explorer™ software package (Applied Biosystems, Framingham, Mass.).

Peptides resulting from digest AspN digests were analyzed by LC-MS using a Hitachi NanoFrontier Mass Spectrometer equipped with NanoLC. Tandem MS of the peptides of interest were analyzed manually.

Additional details of the above-mentioned examples are set forth in numerous references, E.g., G. Srinivasan, C. M. James, J. A. Krzycki, *Science* 2002, 296, 1459; H. Neumann, S, Y. Peak-Chew, J. W. Chin, *Nat Chem Biol* 2008, 4, 232; L. Wang, A. Brock, B. Herberich, P. G. Schultz, *Science* 2001, 292, 498; P, R. Chen, D. Groff, J. Guo, W. Ou, S. Cellitti, B. H. Geierstanger, P. G. Schultz, *Angew Chem Int Ed Engl* 2009, 48, 4052.

Discussion

In summary, Applicants have devised numerous methods, systems and cells for the genetic incorporation of multiple NAAs into a protein. Applicants have also applied various embodiments of such methods, cells and systems to successfully incorporate three copies of AcK into GFP$_{UV}$ in *E. coli*. To Applicants' knowledge, this is the first report that demonstrated the synthesis of a protein with three acetylations in *E. coli* live cells.

However, Applicants note that the scope of the present disclosure is not limited to the above-mentioned studies or findings. For instance, besides the incorporation of multiple copies of AcK into a protein, the developed methods, cells and systems of the present disclosure can be used to incorporate multiple copies of other genetically encoded NAAs into single proteins.

Furthermore, Applicants envision that the methods, cells and systems of the present disclosure can have numerous applications. For instance, in some embodiments, the teachings of the present disclosure can be generally applied to synthesize proteins with multiple posttranslational modifications (e.g., proteins with multiple acetylations) for the functional investigation of those proteins. In additional embodiments, the amber suppression improvement achieved by the reported approach can also, be used to increase expression yield of NAA-incorporated proteins in *E. coil*. Since the genetic NAA incorporation has been applied for constructing therapeutic proteins, the application of this approach in therapeutic protein production is also anticipated.[21]

Another potential application of the reported approach is to use it to achieve the incorporation of two distinct NAAs. Applicants are currently pursuing encoding two distinct NAAs in one protein by amber and ochre stop codons, respectively. Since the translation termination at the ochre stop codon is also partly mediated by RF1, Applicants envision that the over-expressions of L11C should enhance both amber and ochre suppression rates and allow the expression of proteins incorporated with two distinct NAAs with reasonable yields. Moreover, Applicants' methods, cells and systems are independent of the ribo-X system developed by Chin et al.[13] However, Applicants envision that the integration of the two methods could further enhance the amber suppression rate and allow the use of amber codon as a regular sense codon.

Without further elaboration, it is believed that one skilled in the art can, using the description herein, utilize the present invention to its fullest extent. The embodiments described herein are to be construed as illustrative and not as constraining the remainder of the disclosure in any way whatsoever. While the preferred embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein,

APPENDIX I-DNA SEQUENCES

Transfer RNA (pylT)[1]:
ggaaacctgatcatgtagatcgaatggactctaaatccgttcagccgggttagattcccggggtttccgcca The lpp promoter:
cccatcaaaaaaatattctcaacataaaaaactttgtgtaatacttgtaacgct The rrnC terminator:
atccttagcgaaagctaaggatttttttta AcKRS:
atgtcagataaaaaaccattagatgttttaatatctgcgacccgggctctggatgtccaggactggcacgctccacaaaatcaagcaccatgaggtctcaaga
agtaaaatatacattgaaatggcgtgtggagaccatcttgttgtgaataattccaggagttgtagaacagccagagcattcagacatcataagtacagaaaa
acctgcaaacgatgtaggggtttcgggcgaggatatcaataatttttctcacaagatcaaccgaaagcaaaaacagtgtgaaagttagggtagtttctgctcca
aaggtcaaaaaagctatgccgaaatcagtttcaagggctccgaagcctctggaaaattctgtttctgcaaaggcatcaacgaacacatccagatctgtacct
tcgcctgcaaaatcaactccaaattcgtctgttcccgcatcggctcctgctccttcacttacaagaagccagcttgatagggttgaggctctcttaagtcca
gaggataaaatttctctgaatatggcaaagcctttcagggaacttgagcctgaacttgtgacaagaagaaaaaacgattttcagcggctctataccaatgat
agagaagactacctcggtaaactcgaacgtgatattacgaaatttttcgtagcaagggtttctggagataaagtctcctatccttattccggcggaatac
gtggagagaatgggtattaataatgatactgaactttcaaaacagatcttccgggtggataaaaatctctgcttgaggccaatggttgccccgactattttc
aactatgcgcgaaaactcgataggatttaccaggcccaataaaaattttcaagtcggaccttgttaccggaaagagtctgacggcaaagagcacctggaag
aatttactatggtgaacttctttcagatgggttcgggatgtactcgggaaaatcttgaagctctcatcaaagagtttctggactatctggaaatcgacttcg
aaatcgtaggagttcctgtatggtctatggggatactcttgatataatgcacggggacctggagctttcttcggcagtcgtcgggccagtttctcttgatag
agaatggggtattgacaaaccatggataggtgcaggttttggtcttgaacgcttgctcaaggttatgcacggctttaaaaacattaagagggcatcaaggtc
cgaatcttactataatgggatttcaaccaatctgtaa L11C:
atgaccaagaccccgccggcagcagttctgctgaaaaaagcggctggtatcaagtctggttccggtaagccgaacaaagacaaagtgggtaaaatttcccgc
gctcagctgcaggaaatcgcgcagaccaaagctgccgacatgactggtgccgacattgaagcgatgactcgctccatcgaaggtactgcacgttccatgggc
ctggtagtggaggactaa GFP1Amber:
atgagtaaaggagaagaactttctcactggagttgtcccaattcttgttgaattagatggtgatgttaatgggcacaaattttctgtcagtggagagggtgaa
ggtgatgcaacatacggaaaacttacccttaaatttatttgcactactggaaaactacctgttccatggccaacacttgtcactactttctcttatggtgtt
caatgcttttcccgttatccggatcacatgaaacggcatgacttttcaagagtgccatgcccgaaggttatgtacaggaacgcactatatctttcaaagat
gacgggaactacaagacgcgtgctgaagtcaagtttgaaggtgatacccttgttaatcgtatcgagttaaaaggtattgatttaaagaagatggaaacatt
ctcggacacaaactcgagtacaactataactcacactaggtatacatcacggcagacaaagaaaagaatggaatcaaagctaacttcaaaattcgccacaac

APPENDIX I-DNA SEQUENCES attgaagatggatccgttcaactagcagaccattatcaacaaaatactccaattggcgatggccctgtccttttaccagacaaccattacctgtcgacacaa
tctgcccttcgaaagatcccaacgaaaagcgtgaccacatggtccttcttgagtttgtaactgctgctgggattacacatggcatggatgaactctacaaa
gagctccatcaccatcaccatcactaa GFP2Amber:
atgagtaaaggagaagaacttttcactggagttgtcccaattcttgttgaattagatggtgatgttaatgggcacaaattttctgtcagtggagaggtgaag
gtgatgcaacatacggaaaacttacccttaaatttatttgcactactggaaaactacctgttccatggccaacacttgtcactactttctcttatggtgttc
aatgcttttcccgttatccggatcacatgaaacggcatgactttttcaagagtgccatgcccgaaggttatgtacaggaacgcactatatctttcaaagatg
acgggaactacaagacgcgtgctgaatcaagtttgaaggtgataccctt gttaatcgtatcgagttaaaaggtattgattttaaagaagatggaaacattct
cggacacaaactcgagtacaactataactcacactaggtatacatcacggcagacaaacaaaagaatggaatcaaagctaacttcaaaattcgccacaacat
tgaagatggatccgttcaactagcagaccattatcaacaaaatactccaattggcgatggccctctccttttaccagacaaccattacctgtcgacatagtc
tgcccttcgaaagatcccaacgaaaagcgtgaccacatggtccttcttgagtttgtaactgctgctgggattacacatggcatggatgaactctacaaaga
gctccatcaccatcaccatcactaa GFP3Amber:
atgagtaaaggagaagaacttttcactggagttgtcccaattcttgttgaattagatggtgatgttaatgggcacaaattttctgtcagtggagaggtgaa
ggtgatgcaacatacggaaaacttacccttaaatttatttgcactactggaaaactacctgttccatggccaacacttgtcactactttctcttatggtgtt
caatgcttttcccgttatccggatcacatgaaacggcatgactttttcaagagtgccatgcccgaaggttatgtacaggaacgcactatatctttcaaagat
gacgggaactacaagacgcgtgctgaatcaagtttgaaggtgataccctt gttaatcgtatcgagttaaaaggtattgattttaaagaagatggaaacattc
tcggacacaaactcgagtacaactataactcacactaggtatacatcacggcagacaaacaaaagaatggaatcaaagctaacttcaaaattcgccacaaca
ttgaagatggatccgttcaactagcagaccttatcaatagaatactccaattggcgatggccctgtccttttaccagacaaccattacctgtcgacatagtc
tgcccttcgaaagatcccaacgaaaagcgtgaccacatggtccttcttgagtttgtaactgctgctgggattacacatggcatggatgaactctacaaaga
gctccatcaccatcaccatcactaa GFP2Amber':
atggcatagtaaaggagaagaacttttcactggagttgtcccaattcttgttgaattagatggtgatgttaatgggcacaaattttctgtcagtggagag
ggtgaaggtgatgcaacatacggaaaacttacccttaaatttatttgcactactggaaaactacctgttccatggccaacacttgtcactactttctcttat
ggtgttcaatgcttttcccgttatccggatcacatgaaacggcatgactttttcaagagtgccatgcccgaaggttatgtacaggaacgcactatatctttc
aaagatgacgggaactacaagacgcgtgctgaagtcaagtttgaaggtgataccctt gttaatcgtatcgagttaaaaggtattgattttaaagaagatgga
aacattctcggacacaaactcgagtacaactataactcacactaggtatacatcacggcagacaaacaaaagaatggaatcaaagctaacttcaaaattcgc
cacaacattgaagatggatccgttcaactagcagaccattatcaacaaaatactccaattggcgatggccctgtccttttaccagacaaccattacctgtcg
acatagtctgcccttcgaaagatcccaacgaaaagcgtgaccacatggtccttcttgagtttgtaactgctgctgggattacacatggcatggatgaactc
tacaaagagctccatcaccatcaccatcactaa

APPENDIX II-PROTEIN SEQUENCES

AcKRS:
msdkkpldvlisatglwmsrtgtlhkikhhevsrskiyiemacgdhlvvnnsrscrtarafrhhkyrktckrcrvsgedinnfltrstesknsvkvrvysap
kykkampksvsrapkplensvsakastntsrsvpspakstpnssvpasapapsltrsqldrveallspedkislnmakpfrelepelvtrrkndfqrlytnd
redylgklerditkffydrgfleikspilipaeyvermginndtelskqifrvdknlclrpmvaptifnyarkldrilpgpikifevgpcyrkesdgkehle
eftmvnffqmgsgctrenlealikefldyleidfeivgdscmvygdtldimhgdlelssavvgpvsldrewgidkpwigagfglerllkvmhgfknikrasr
sesyyngistnl L11C:
mtktppaavllkkaagiksgsgkpnkdkvgkisraqlqeiaqtkaadmtgadieamtrsiegtarsmglvved GFP1Amber:
mskgeelftgvvpilveldgdvnghkfsvsgegegdatygkltlkficttgklpvpwptlvttfsygvqcfsrypdhmkrhdffksampegyvqertisfkd
dgnyktraevkfegdtlvnrielkgidfkedgnilghkleynynshk*vyitadkqkngikanfkirhniedgsvqladhyqqntpigdgpvllpdnhylst
qsalskdpnekrdhmvllefvtaagithgmdelykelhhhhhh GFP2Amber:
mskgeelftgvvpilveldgdvnghkfsvsgegegdatygkltlkficttgklpvpwptlvttffsygvqcfsrypdhmkrhdffksampegyvqertisfkd
dgnyktraevkfegdtlvnrielkgidfkedgnilghkleynynshk*vyitadkqkngikanfkirhniedgsvqladhyqqntpigdgpvllpdnhylst
k*salskdpnekrdhmvllefvtaagithgmdelykelhhhhhh GFP3Amber:
mskgeelftgvvpilveldgdvnghkfsvsgegegdatygkltlkficttgklpvpwptlvttfsygvqcfsrypdhmkrhdffksampegyvqertisfkd
dgnyktraevkfegdtlvnrielkgidfkedgnilghkleynynshk*vyitadkqkngikanfkirhniedgsvqladhyqk*ntpigdgpvllpdnhyls
tk*salskdpnekrdhmvllefvtaagithgmdelykelhhhhhh GFP2Amber':
mak*skgeelftgvvpilveldgdvnghkfsysgegegdatygkltlkficttgklpvpwptlvttfsygvqcfsrypdhmkrhdffksampegyvqertis
fkddgnyktraevkfegdtlvnrielkgidfkedgnilghkleynynshk*vyitadkqkngikanfkirhniedgsvqladhyqqntpigdgpvllpdnhy
lstqsalskdpnekrdhmvllefvtaagithgmdelykelhhhhhh.

CITED REFERENCES

[1] C. T. Walsh, S. Garneau-Tsodikova, G. J. Gatto, Jr., *Angew Chem Int Ed Engl* 2005, 44, 7342.
[2] C. T. Walsh, *Posttranslational Modification of Proteins: Expanding Nature's Inventory*, Roberts & Company Publishers, Englewood, Colo., 2005.
[3] L. Wang, J. Xie, P. G. Schultz, *Annu Rev Biophys Biomol Struct* 2006, 35, 225.
[4] L. Wang, P. G. Schultz, *Angew Chem Int Ed Engl* 2004, 44, 34.
[5] L. Wang, A. Brock, B. Herberich, P. G. Schultz, *Science* 2001, 292, 498.

[6] J. W. Chin, T. A. Cropp, J. C. Anderson, M. Mukherji, Z. Zhang, P. G. Schultz, *Science* 2003, 301, 964.
[7] W. Liu, A. Brock, S. Chen, P. G. Schultz, *Nat Methods* 2007, 4, 239.
[8] Z. Zhang, J. Gildersleeve, Y. Y. Yang, R. Xu, J. A. Loo, S. Uiyu, C. H. Wong, P. G. Schultz, *Science* 2004, 303, 371.
[9] C. C. Liu, P. G. Schultz, *Nat Biotechnol* 2006, 24, 1436.
[10] C. C. Liu, E. Brustad, W. Liu, P. G. Schultz, *J Am Chem Soc* 2007, 129, 10648.
[11] H. Neumann, S. Y. Peak-Chew, J. W. Chin, *Nat Chem Biol* 2008, 4, 232.
[12] S. Lall, *Nat Struct Mol Biol* 2007, 14, 1110.
[13] K. Wang, H. Neumann, S. Y. Peak-Chew, J. W. Chin, *Nat Biotechnol* 2007, 25, 770.
[14] N. Van Dyke, E. J. Murgola, *J Mol Biol* 2003, 330, 9.
[15] U. Rawat, H. Gao, A. Zavialov, R. Gursky, M. Ehrenberg, J. Frank, *J Mol Biol* 2006. 357, 1144.
[16] S. Petry, D. E. Brodersen, F. V. t. Murphy, C. M. Dunham, M. Selmer, M. J. Tarry, A. C. Kelley, V. Ramakrishnan, *Cell* 2005, 123, 1255.
[17] M. Laurberg, H. Asahara, A. Korostelev, J. Zhu, S. Trakhanov, H. F. Noller, *Nature* 2008, 454, 852.
[18] L. Bouakaz, E. Bouakaz, E. J. Murgola, M. Ehrenberg, S. Sanyal, *J Biol Chem* 2006, 281. 4548
[19] T. Mukai, T. Kobayashi, N. Hina, T. Yanagisawa, K. Sakamoto, S. Yokoyama, *Biochem Biophys Res Commun* 2008, 371, 818.
[20] Personal discussion with Dr. Jianming Xie and Dr. Jiantao Guo.
[21] R. F. Service, *Science* 2005, 308, 44.

What is claimed is:

1. A method of incorporating a non-canonical amino acid into a protein during a translation of said protein in bacterial cells, said method comprising:
providing a modified ribosome in said bacterial cells, wherein said modified ribosome comprises a truncated L11 protein, wherein said truncated L11 protein in said modified ribosome is truncated at the first 72 amino acids of N-terminus of the L-11 protein;
providing a nucleotide sequence in said bacterial cells, wherein said nucleotide sequence encodes said protein, and
wherein said nucleotide sequence comprises an introduced stop codon at a site where said incorporation of said non-canonical amino acid into said protein is desired;
providing a suppressor transfer RNA in said bacterial cells, wherein said suppressor transfer RNA is acylated with said non-canonical amino acid, and
wherein the anti-codon of said suppressor transfer RNA recognizes said introduced stop codon in said nucleotide sequence; and
wherein a translation of said transcript by said modified ribosome and said suppressor transfer RNA incorporates said non-canonical amino acid into said translated protein.

2. The method of claim 1, wherein said modified ribosome is provided by over-expressing said truncated L11 protein in said bacterial cells.

3. The method of claim 1, wherein said modified ribosome is provided by genetically knocking out the first 72 amino acids of the N-terminal domain of the L-11 protein from the bacterial genome.

4. The method of claim 1, wherein said non-canonical amino acid is a posttranslationally modified canonical amino acid.

5. The method of claim 1, wherein said non-canonical amino acid is a non-natural amino acid, and wherein said non-canonical amino acid is incorporated into said protein by nonsense suppression.

6. The method of claim 1, wherein said non-canonical amino acid is selected from the group consisting of O-sulfo-L-tyrosine, O-phospho-L-tyrosine, m-nitro-L-tyrosine, $N^\epsilon$-methyl-L-lysine $N^\epsilon$, $N^\epsilon$-dimethyl-lysine, $N^\epsilon,N^\epsilon,N^\epsilon$-trimethyl-lysine, $N^\epsilon$-succinyl-L-lysine, $N^\epsilon$-malonyl-L-lysine, $N^\epsilon$-acetyl-L-lysine (AcK), p-azido-L-phenylalanine, p-benzoyl-L-phenylalanine, p-propargyloxy-L-phenylalanine, p-iodo-Lphenylalanine, p-acetyl-L-phenylalanine, p-nitro-L-phenylalanine, p-(1',3'-dioxobutyl)-L-phenylalanine, Se-phenyl-L-selenocysteine, 4'-[3-(trifluoromethyl)-3H-diazirin-3-yl]-1-phenylalanine, O-nitrobenzyl-L-tyrosine, p-(phenylazo)-L-phenylalanine, p-carboxymethyl-L-phenylalanine, (S)-2-amino-4-(7-hydroxy-2-oxo-2H-chromen-4-yl)butanoic acid, p-bromo-L-phenylalanine, O-methyl-L-tyrosine, p-cyano-L-phenylalanine, m-cyano-L-phenylalanine, 3,4- dihydroxy -L-phenylalanine, 3-amino-L-tyrosine, p-amino-L-phenylalanine, (S)-3-(2,2$^1$-bipyridin-5-yl)-2-aminopropanoic acid, 3-(8-hydroxyquinolin-3-yl)-L-alanine, $N^\epsilon$-(t-butylcarbamoyl)-L-lysine, $N^\epsilon$-propargyloxycarbonyl-L-lysine, $N^\epsilon$-(2-azidoethyloxycarbonyl)-L-lysine, $N^\epsilon$-(o-nitrobenzyloxycarbonyl)-L-lysine, $N^\epsilon$-(o-nitrobenzyloxycarbonyl)- $N^\epsilon$-methyl-L- lysine, $N^\epsilon$-(benzyloxycarbonyl)-L-lysine, $N^\epsilon$-(benzyloxycarbonyl)-$N^\epsilon$-methy-L-lysine, $N^\epsilon$-(L-cysteinyl)-L-lysine, $N^\epsilon$-(D-cysteinyl)-L-lysine, and L-2-amino-8-oxononanic acid.

7. The method of claim 1, wherein said bacterial cells are *E. coil* cells.

8. The method of claim 1, wherein said nucleotide sequence is part of an expression vector, and wherein said nucleotide sequence is provided to said bacterial cells by transforming said bacterial cells with said expression vector.

9. The method of claim 8, wherein said expression vector is an IPTG-inducible plasmid.

10. The method of claim 9, wherein said plasmid is pET-Duet-1.

11. The method of claim 1, wherein said introduced stop codon in said nucleotide sequence is an ochre or amber stop codon.

12. The method of claim 11, wherein said introduced stop codon is an amber stop codon.

13. The method of claim 1, wherein said method incorporates a plurality of non-canonical amino acids into said protein, and wherein said method further comprises:
providing a plurality of introduced stop codons in said nucleotide sequence,
wherein said introduced stop codons are at sites where said incorporation of said plurality of non-canonical amino acids into said protein is desired,
wherein the anti-codon of said suppressor transfer RNA recognizes one or more of said introduced stop codons, and
wherein the number of the plurality of introduced stop codons is 1, 2 or 3.

14. The method of claim 13, wherein three non-canonical amino acids are incorporated into said protein, and wherein said nucleotide sequence comprises three introduced stop codons at sites where said incorporation of said three non-canonical amino acids into said protein is desired.

15. The method of claim 13, wherein said plurality of non-canonical amino acids are distinct non-canonical amino acids, and wherein said method further comprises:
providing a plurality of suppressor transfer RNAs,
wherein each of said plurality of suppressor transfer RNAs is acylated with a distinct non-canonical amino acid, and
wherein the anti-codon of each of said suppressor transfer RNAs recognizes one or more of said introduced stop codons in said nucleotide sequence.

* * * * *